United States Patent
Young et al.

(10) Patent No.: US 7,507,537 B2
(45) Date of Patent: *Mar. 24, 2009

(54) CYTOTOXICITY MEDIATION OF CELLS EVIDENCING SURFACE EXPRESSION OF CD44

(75) Inventors: David S. F. Young, Toronto (CA); Susan E. Hahn, Toronto (CA); Helen P. Findlay, Toronto (CA)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/592,516

(22) Filed: Nov. 3, 2006

(65) Prior Publication Data

US 2007/0053836 A1 Mar. 8, 2007

Related U.S. Application Data

(63) Continuation of application No. 10/810,165, filed on Mar. 26, 2004, now abandoned, which is a continuation-in-part of application No. 10/647,818, filed on Aug. 22, 2003, now Pat. No. 7,189,397, which is a continuation-in-part of application No. 10/603,000, filed on Jun. 23, 2003, now Pat. No. 7,252,821, which is a continuation-in-part of application No. 09/727,361, filed on Nov. 29, 2000, now Pat. No. 6,657,048, which is a continuation-in-part of application No. 09/415,278, filed on Oct. 8, 1999, now Pat. No. 6,180,357.

(51) Int. Cl.
*A61K 39/395* (2006.01)
*A61K 51/00* (2006.01)

(52) U.S. Cl. .................. 435/6; 424/1.49; 424/155.1

(58) Field of Classification Search ............. 435/6; 424/1.49, 155.1
See application file for complete search history.

(56) References Cited

U.S. PATENT DOCUMENTS

| | | | |
|---|---|---|---|
| 4,861,581 A | 8/1989 | Epstein et al. | |
| 5,171,665 A | 12/1992 | Hellstrom et al. | |
| 5,484,596 A | 1/1996 | Hanna, Jr. et al. | |
| 5,616,468 A | 4/1997 | Salmi et al. | |
| 5,693,763 A | 12/1997 | Codington et al. | |
| 5,750,102 A | 5/1998 | Eisenbach et al. | |
| 5,780,033 A | 7/1998 | Torchilin et al. | |
| 5,783,186 A | 7/1998 | Arakawa et al. | |
| 5,849,876 A | 12/1998 | Linsley et al. | |
| 5,869,045 A | 2/1999 | Hellstrom et al. | |
| 5,869,268 A | 2/1999 | Kudo et al. | |
| 5,879,898 A | 3/1999 | Tarin et al. | |
| 5,885,575 A | 3/1999 | Herrlich et al. | |
| 5,916,561 A | 6/1999 | Adolf et al. | |
| 5,942,417 A | 8/1999 | Ni et al. | |
| 6,180,357 B1 | 1/2001 | Young et al. | |
| 6,657,048 B2 | 12/2003 | Young et al. | |
| 7,189,397 B2 * | 3/2007 | Young et al. ............. | 424/156.1 |
| 2003/0103985 A1 | 6/2003 | Adolf et al. | |
| 2004/0001789 A1 | 1/2004 | Young et al. | |
| 2004/0105815 A1 | 6/2004 | Young et al. | |
| 2005/0008646 A1 | 1/2005 | Young et al. | |

FOREIGN PATENT DOCUMENTS

| | | |
|---|---|---|
| WO | WO94/12631 | 6/1994 |
| WO | WO02/094879 | 11/2002 |
| WO | WO2003/055515 | 7/2003 |

OTHER PUBLICATIONS

ATCC search for PTA-4621 hybridoma deposit.*
Chatterjee et al Cancer Immunol. Imunother., 1994, 75-82.*
Gura et al (Science vol. 278 Nov. 1997 1041-1042).*
Seaver (1994; Genetic Engineering vol. 14(14): pp. 10 and 21).*
Rudikoff et al (Proc Natl Acad Sci USA 1982 vol. 79 p. 1979).*
Voskoglou-Nomikos (Clin. Can. Res. 9:4227-4239 (2003)).*
Dennis (Nature 442:739-741 (2006)).*
M. Allouche et al, "Ligation of the CD44 adhesion molecule inhibits drug-induced apoptosis in human myeloid leukemia cells", Blood, 96(3):1187-1190 (Aug. 2000).
I. Barshack et al, CD44 expression in normal adrenal tissue and adrenal tumors, J. Clin. Pathol., 51:52-54 (1998).
R. Breyer et al, "Disruption of Intracerebral progression of C6 rat glioblastoma by in vivo treatment with anti-CD44 monoclonal antibody", J. Neurosurg., 92:140-149 (Jan. 2000).
D. Colnot et al, "Reinfusion of unprocessed, granulocyte colony-stimulating factor-stimulated whole blood allows dose escalation of 186relabeled chimeric monoclonal antibody U36 radioimmunotherapy in a phase I dose escalation study", Clin. Cancer Res., 8:3401-3406 (Nov. 2002).
D. Colnot et al, "Radioimmunotherapy in patients with head and neck squamous cells carcinoma:initial experience", Head & Neck, 23:559-565 (Jul. 2001).

(Continued)

*Primary Examiner*—David J. Blanchard
*Assistant Examiner*—Lynn Bristol
(74) *Attorney, Agent, or Firm*—McHale & Slavin, P.A.

(57) ABSTRACT

This invention relates to the diagnosis and treatment of cancerous diseases, particularly to the mediation of cytotoxicity of tumor cells; and most particularly to the use of cancerous disease modifying antibodies (CDMAB) or derivatives thereof, optionally in combination with one or more chemotherapeutic agents, as a means for initiating the cytotoxic response. The invention further relates to binding assays which utilize the CDMABs of the instant invention.

18 Claims, 8 Drawing Sheets

(4 of 8 Drawing Sheet(s) Filed in Color)

OTHER PUBLICATIONS

D. Colnot et al, "Phase I therapy study of 186Re-labeled chimeric monoclonal antibody U36 in patients with squamous cell carcinoma of the head and neck", J. Nucl. Med., 41:1999-2010 (Dec. 2000).

D. Colnot et al, "Evaluation of limited blood sampling in a preceding 99mTC-labeled diagnostic study to predict the pharmacokinetics and myelotoxicity of 186Re-cMAb U36 radioimmunotherapy", J. Nucl. Med., 42 (9):1364-1367 (Sep 2001).

A. Daar et al, "The membrane antigens of human colorectal cancer cells:demonstration with monoclonal antibodies of heterogeneity within and between tumours and of anomalous expression of HLA-DR", Eur. J. Cancer Clin. Oncol., 19(2):209-220 (1983).

R. De Bree et al, "Selection of monoclonal antibody E48 IgG or U36 IgG for adjuvant radioimmunotherapy in head and neck cancer patients", British J. Cancer, 75(7):1049-1060 (1997).

R. De Bree et al, "Radioimmunoscintigraphy and biodistribution of technetium-99m-labeled monoclonal antibody U36 in patients with head and neck cancer", Clin. Can. Res., 1:591-598 (Jun. 1995).

S. Denning et al, "Antibodies against the CD44 p80, lymphocyte homing receptor molecule augment human peripheral blood T cell activation", J. Immunol., 144:7-15 (Jan. 1990).

B. Flanagan et al, "Chemical composition and tissue distribution of the human CDw44 glycoprotein", Immunol., 67:167-175 (1989).

S. Fox et al, "Normal human tissues, in addition to some tumors, express multiple different CD44 isoforms", Cancer Res., 54:4539-4546 (Aug. 1994).

U. Gunthert et al, "A new variant of glycoprotein CD44 confers metastatic potential to rat carcinoma cells", Cell, 65:13-24 (Apr. 1991).

Y. Guo et al, "Inhibition of human melanoma growth and metastasis in vivo by anti-CD44 monoclonal antibody", Cancer Res., 54:1561-1565 (Mar. 1994).

K. Heider et al, "Differential expression of CD44 splice variants in intestinal- and diffuse-type human gastric carcinomas and normal gastric mucosa", Cancer Res., 53:4197-4203 (Sep. 1993).

K. Heider et al, "A human homologue of the rat metastasis-associated variant of CD44 is expressed in colorectal carcinomas and adenomatous polyps", J. Cell Biol., 120:27-233 (Jan. 1993).

K. Heider et al, "Splice variants of the cell surface glycoprotein CD44 associated with metastatic tumour cells are expressed in normal tissues of humans and cynomolgus monkeys", Eur. J. Cancer, 31A(13/14):2385-2391 (1995).

K. Heider et al, "Characterization of high-affinity monoclonal antibody specific for CD44v6 as candidate for immunotherapy of squamous cell carcinomas", Cancer Immunol. Immunother., 43:245-253 (1996).

S. Jalkanen et al, "Biochemical properties of glycoproteins involved in lymphocyte recognition of high endothelial venules in man", J. Immunol., 141:1615-1623 (Sep. 1988).

S. Kayastha et al, "Expression of the hyaluronan receptor, CD44S, in epithelial ovarian cancer is an independent predictor of survival", Clin. Cancer Res., 5:1073-1076 (May 1999).

S. Kennel et al, "CD44 expression on murine tissues", J. Cell Science, 104:373-382 (1993).

M. Khoursheed et al, "Expression of CD44s in human colorectal cancer", Pathology Oncology Research, 8 (3):170-174 (2002).

G. Koopman et al, "Activated human lymphocytes and aggressive non-hodgkins's lymphomas express a homologue of the rat metastasis-associated variant of CD44", J. Exp. Med., 177:897-904 (Apr. 1993).

M. Kuppner et al, "Differential expression of the CD44 molecule in human brain tumours", Int. J. Cancer, 50:572-577 (1992).

C. Mackay et al, "Expression and modulaton of CD44 variant isoforms in humans", J. Cell Biol., 124:71-82 (Jan. 1994).

D. Noar et al, "CD44 in cancer", Critical Reviews in Clinical Laboratory Science, 39(6):527-579 (2002).

H. Ponta et al, "CD44: from adhesion molecules to signaling regulators", Nature Reviews, Molelcular Cell Biology, 4:33-45 (Jan. 2003).

J. Ross et al, "Expression of the CD44 cell adhesion molecule in urinary bladder transitional cell carcinoma", Mod. Pathol., 9(8):854-860 (1996).

M. Sami et al, "Regulated expression of exon v6 containing isoforms of CD44 in man: downregulation during malignant transformation of tumors of squamocellular origin", J. Cell Biol., 122(2):431-442 (Jul. 1993).

A. Schrijvers et al, "MAb U36, a novel monoclonal antibody successful in immunotargeting of squamous cell carcinoma of the head and neck", Cancer Res., 53:4383-4390 (Sep. 1993).

S. Seiter et al, "Prevention of tumor metastasis formation by anti-variant CD44", J. Exp. Med., 177:443-455 (Feb. 1993).

Y. Shimizu et al, "Dual role of the CD44 molecule in T cell adhesion and activation", J. Immunol., 143:2457-2463 (Oct. 1989).

T. Strobel et al, "In vivo inhibition of CD44 limits intra-abdominal spread of a human ovarian cancer xenograft in nude mice: a novel role for CD44 in the process of peritoneal implantation", Cancer Res., 57:1228-1232 (Apr. 1997).

J. Stroomer et al, "Safety and biodistribution of 99m Technetium-labeled anti-CD44v6 monoclonal antibody BIWA 1 in head and neck cancer patients", Clin. Can. Res., 6:3046-3055 (Aug. 2000).

N. Van Hal et al, "Monoclonal antibody U36, a suitable candidate for clinical immunotherapy of squamous-cell carcinoma, recognizes a CD44 isoform", Int. J. Cancer, 68:520-527 (1996).

S. Wallach-Dayan et al, "CD44-dependent lymphoma cell dissemination: a cell surface CD44 variant, rather than standard CD44, supports in vitro lymphoma cell rolling on hyaluronic acid substrate and its in vivo accumulation in the peripheral lymph nodes", J. Cell Science, 114:3463-3477 (2001).

M. Zahalka et al, "Lymph node (but not spleen) invasion by murine lymphoma is both CD44- and hyaluronate-dependent", J. Immunol., 154:5345-5355 (1995).

V. Zawadzki et al, "blockade of metastasis formation by CD44-receptor globulin", Int. J. Cancer, 75:919-924 (1998).

D. Young et al, "ARH460-16-2: A therapeutic monoclonal antibody targeting CD4 in Her2/neu negative breast cancer", Journal of Clinical Oncology, 22:193s (Jul. 2004) Abstract 2622.

A. Seth et al, "T-cell-receptor-independent activation of cytolytic activity of cytotoxic T lymphocytes mediated through CD44 and gp90MEL-14", Proc. Natl. Acad. Sci. USA, 88:7877-7881 (Sep. 1991).

S. Seaver, "Monoclonal antibodies in industry: more difficult than orginally thought", Genetic Engineering, 14 (14):10 and 21 (1994).

S. Rudikoff et al, "Single amino acid substitution altering antigen-binding specificity", Proc. Natl. Acad. Sci. USA, 79:1979-1983 (Mar. 1982).

Fundamental Immunology, Chapter 8: Immunogenicity and Antigen Structure, William E. Paul, M.D. ed., 3d ed, p. 242 Raven Press, NY (1993).

R. Johnson et al, "The clinical impact of screening and other experimental tumor studies", Cancer Treatment Review, 2:1-31 (1975).

Bectin Dickinson Technical Data Sheet for L178 Clone (published Nov. 5, 2003).

T. Gura, "Systems for identifying new drugs are often faulty", Science, 278:1041-1042 (Nov. 1997).

M. Chatterjee et al, "Idiotypic antibody immunotherapy of cancer", Cancer Immunol Immunother., 38:75-82 (1994).

R. Galandrini et al, "CD44 Triggering enhances human NK cell cytotoxic functions", J. Immunol., 153:4399-4407 (1994).

* cited by examiner

CYTOTOXICITY MEDIATION OF CELLS EVIDENCING SURFACE EXPRESSION OF CD44

REFERENCE TO RELATED APPLICATIONS

This application is a continuation of application Ser. No. 10/810,165 filed Mar. 26, 2004, now abandoned, which is a continuation-in-part of application Ser. No. 10/647,818 filed Aug. 22, 2003, now U.S. Pat. No. 7,189,397B1, which is a continuation-in-part of application Ser. No. 10/603,000, filed Jun. 23, 2003, now U.S. Pat. No. 7,252,821B1, which is a continuation-in-part of application Ser. No. 09/727,361, filed Nov. 29, 2000, now U.S. Pat. No. 6,657,048B1, which is a continuation-in-part of application Ser. No. 09/415,278, filed Oct. 8, 1999, now U.S. Pat. No. 6,180,357B1, the contents of each of which are herein incorporated by reference.

FIELD OF THE INVENTION

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays, which utilize the CDMAB of the instant invention.

BACKGROUND OF THE INVENTION

Raising monoclonal antibodies against human white blood cells led to the discovery of the CD44 antigen; a single chain hyaluronic acid (HA) binding glycoprotein expressed on a wide variety of normal tissue and on all types of hematopoietic cells. It was originally associated with lymphocyte activation and homing. Currently, its putative physiological role also includes activation of inflammatory genes, modulation of cell cycle, induction of cell proliferation, induction of differentiation and development, induction of cytoskeletal reorganization and cell migration and cell survival/resistance to apoptosis.

In humans, the single gene copy of CD44 is located on the short arm of chromosome 11, 11p13. The gene contains 19 exons; the first 5 are constant, the next 9 are variant, the following 3 are constant and the final 2 are variant. Differential splicing can lead to over 1000 different isoforms. However, currently only several dozen naturally occurring variants have been identified.

The CD44 standard glycoprotein consists of a N-terminal extracellular (including a 20 a.a. leader sequence, and a membrane proximal region (85 a.a.)) domain (270 a.a.), a transmembrane region (21 a.a.) and a cytoplasmic tail (72 a.a.). The extracellular region also contains a link module at the N-terminus. This region is 92 a.a. in length and shows homology to other HA binding link proteins. There is high homology between the mouse and human forms of CD44. The variant forms of the protein are inserted to the carboxy terminus of exon 5 and are located extracellularly when expressed.

A serum soluble form of CD44 also occurs naturally and can arise from either a stop codon (within the variable region) or from proteolytic activity. Activation of cells from a variety of stimuli including TNF-α results in shedding of the CD44 receptor. Shedding of the receptor has also been seen with tumor cells and can result in an increase in the human serum concentration of CD44 by up to 10-fold. High CD44 serum concentration suggests malignancy (ovarian cancer being the exception).

The standard form of CD44 exists with a molecular weight of approximately 37 kD. Post-translational modifications increase the molecular weight to 80-90 kD. These modifications include amino terminus extracellular domain N-linked glycosylations at asparagine residues, O-linked glycosylations at serine/threonine residues at the carboxy terminus of the extracellular domain and glycosaminoglycan additions. Splice variants can range in size from 80-250 kD.

HA, a polysaccharide located on the extracellular matrix (ECM) in mammals, is thought to be the primary CD44 ligand. However, CD44 has also been found to bind such proteins as collagen, fibronectin, laminin etc. There appears to be a correlation between HA binding and glycosylation. Inactive CD44 (does not bind HA) has the highest levels of glycosylation, active CD44 (binding HA) the lowest while inducible CD44 (does not or weakly binds HA unless activated by cytokines, monoclonal antibodies, growth factors, etc.) has glycoslyation levels somewhere in between the active and inactive forms.

CD44 can mediate some of its functions through signal transduction pathways that depend on the interaction of the cell, stimulus and the environment. Some of these pathways include the NFκB signaling cascade (involved in the inflammatory response), the Ras-MAPK signal transduction pathway (involved with activating cell cycling and proliferation), the Rho family of proteins (involved with cytoskeleton reorganization and cell migration) and the PI3-K-related signaling pathway (related to cell survival). All of the above-mentioned functions are closely associated with tumor disease initiation and progression. CD44 has also been implicated in playing a role in cancer through a variety of additional mechanisms. These include the presentation of growth factors, chemokines and cytokines by cell surface proteoglycans present on the cell surface of CD44 to receptors involved in malignancy. Also, the intracellular degradation of HA by lysosomal hylauronidases after internalization of the CD44-HA complex can potentially increase the likelihood of tumor invasiveness and induction of angiogenesis through the ECM. In addition, the transmission of survival or apoptotic signals has been shown to occur through either the standard or variable CD44 receptor. CD44 has also been suggested to be involved in cell differentiation and migration. Many, if not all, of these mechanisms are environment and cell dependent and several give rise to variable findings. Therefore, more research is required before any conclusions can be drawn.

In order to validate a potential functional role of CD44 in cancer, expression studies of CD44 were undertaken to determine if differential expression of the receptor correlates with disease progression. However, inconsistent findings were observed in a majority of tumor types and this is probably due to a combination of reagents, technique, pathological scoring and cell type differences between researchers. Renal cell carcinoma and non-Hodgkin's lymphoma appear to be the exception in that patients with high CD44 expressing tumors consistently had shorter survival times than their low or non-CD44 expressing counterparts.

Due to its association with cancer, CD44 has been the target of the development of anti-cancer therapeutics. There is still controversy as to whether the standard or the variant forms of CD44 are required for tumor progression. There is in vivo animal data to support both views and again it may be tumor type and even cell type dependent. Different therapeutic approaches have included injection of soluble CD44 proteins, hyaluronan synthase cDNA, hyaluronidase, the use of CD44 antisense and CD44 specific antibodies. Each approach has led to some degree of success thereby providing support for anti-CD44 cancer therapeutics.

Both variant and standard CD44 specific monoclonal antibodies have been generated experimentally but for the most part these antibodies have no intrinsic biological activity, rather they bind specifically to the type of CD44 they recognize However, there are some that are either active in vitro or in vivo but generally not both. Several anti-CD44 antibodies have been shown to mediate cellular events. For example the murine antibody A3D8, directed against human erythrocyte Lutheran antigen CD44 standard form, was shown to enhance CD2 (9-1 antibody) and CD3 (OKT3 antibody) mediated T cell activation; another anti-CD44 antibody had similar effects. A3D8 also induced IL-1 release from monocytes and IL-2 release from T lymphocytes. Interestingly, the use of A3D8 in conjunction with drugs such as daunorubicin, mitoxantrone and etoposide inhibited apoptosis induction in HL60 and NB4 AML cells by abrogating the generation of the second messenger ceramide. The J173 antibody, which does not have intrinsic activity and is directed against a similar epitope of CD44s, did not inhibit drug-induced apoptosis. The NIH44-1 antibody, directed against an 85-110 kD and 200 kD form of CD44, augmented T-cell proliferation through a pathway the authors speculated as either cross-linking or aggregation of CD44. Taken together, there is no evidence that antibodies such as these are suitable for use as cancer therapeutics since they either are not directed against cancer (e.g. activate lymphocytes), induce cell proliferation, or when used with cytotoxic agents inhibited drug-induced death of cancer cells.

Several anti-CD44 antibodies have been described which demonstrate anti-tumor effects in vivo. The antibody 1.1ASML, a mouse IgG1 directed to the v6 variant of CD44, has been shown to decrease the lymph node and lung metastases of the rat pancreatic adenocarcinoma BSp73ASML. Survival of the treated animals was concomitantly increased. The antibody was only effective if administered before lymph node colonization, and was postulated to interfere with cell proliferation in the lymph node. There was no direct cytototoxicy of the antibody on the tumor cells in vitro, and the antibody did not enhance complement-mediated cytotoxicity, or immune effector cell function. Utility of the antibody against human cells was not described.

Breyer et al. described the use of a commercially-available antibody to CD44s to disrupt the progression of an orthotopically-implanted rat glioblastoma. The rat glioblastoma cell line C6 was implanted in the frontal lobe, and after 1 week, the rats were given 3 treatments with antibody by intracerebral injection. Treated rats demonstrated decreased tumor growth, and higher body weight than buffer or isotype control treated rats. The antibody was able to inhibit adhesion of cells in vitro to coverslips coated with extracellular matrix components, but did not have any direct cytotoxic effects on cells. This antibody was not tested against human cells.

A study was carried out which compared the efficacy of an antibody to CD44s (IM-7.8.1) to an antibody to CD44v10 (K926). The highly metastatic murine melanoma line B16F10, which expresses both CD44 isoforms, was implanted intraveinously into mice. After 2 days, antibodies were given every third day for the duration of the study. Both antibodies caused a significant reduction of greater than 50% in the number of lung metastases; there was no significant difference in efficacy between the two antibodies. The antibody did not affect proliferation in vitro, and the authors, Zawadzki et al., speculated that the inhibition of tumor growth was due to the antibody blocking the interaction of CD44 with its ligand. In another study using IM-7.8.1, Zahalka et al. demonstrated that the antibody and its F(ab')$_2$ fragment were able to block the lymph node infiltration by the murine T-cell lymphoma LB. This conferred a significant survival benefit to the mice. Wallach-Dayan et al. showed that transfection of LB-TRs murine lymphoma, which does not spontaneously form tumors, with CD44v4-v10 conferred the ability to form tumors. IM-7.8.1 administration decreased tumor size of the implanted transfected cells in comparison to the isotype control antibody. None of these studies demonstrated human utility for this antibody.

GKW.A3, a mouse IgG2a, is specific for human CD44 and prevents the formation and metastases of a human melanoma xenograft in SCID mice. The antibody was mixed with the metastastic human cell line SMMU-2, and then injected subcutaneously. Treatments were continued for the following 3 weeks. After 4 weeks, only 1 of 10 mice developed a tumor at the injection site, compared to 100 percent of untreated animals. F(ab')$_2$ fragments of the antibody demonstrated the same inhibition of tumor formation, suggesting that the mechanism of action was not dependent on complement or antibody-dependent cellular cytotoxicity. If the tumor cells were injected one week prior to the first antibody injection, 80 percent of the animals developed tumors at the primary site. However, it was noted that the survival time was still significantly increased. Although the delayed antibody administration had no effect on the primary tumor formation, it completely prevented the metastases to the lung, kidney, adrenal gland, liver and peritoneum that were present in the untreated animals. This antibody does not have any direct cytotoxicity on the cell line in vitro or does it interfere with proliferation of SMMU-2 cells, and appears to have its major effect on tumor formation by affecting metastasis or growth. One notable feature of this antibody was that it recognized all isoforms of CD44, which suggests limited possibilities for therapeutic use.

Strobel et al. describe the use of an anti-CD44 antibody (clone 515) to inhibit the peritoneal implantation of human ovarian cancer cells in a mouse xenograft model. The human ovarian cell line 36M2 was implanted intraperitoneally into mice in the presence of the anti-CD44 antibody or control antibody, and then treatments were administered over the next 20 days. After 5 weeks, there were significantly fewer nodules in the peritoneal cavity in the antibody treated group. The nodules from both the anti-CD44 and control treated groups were the same size, suggesting that once the cells had implanted, the antibody had no effect on tumor growth. When cells were implanted subcutaneously, there was also no effect on tumor growth, indicating that the antibody itself did not have an anti-proliferative or cytotoxic effect. In addition, there was no effect of the antibody on cell growth in vitro.

VFF-18, also designated as BIWA 1, is a high-affinity antibody to the v6 variant of CD44 specific for the 360-370 region of the polypeptide. This antibody has been used as a $^{99m}$Technetium-labelled conjugate in a Phase 1 clinical trial in 12 patients. The antibody was tested for safety and targeting potential in patients with squamous cell carcinoma of the head and neck. Forty hours after injection, 14 percent of the injected dose was taken up by the tumor, with minimal accumulation in other organs including the kidney, spleen and bone marrow. The highly selective tumor binding suggests a role for this antibody in radioimmunotherapy, although the exceptionally high affinity of this antibody prevented penetration into the deeper layers of the tumor. Further limiting the application of BIWA 1 is the immunogenicity of the murine antibody (11 of 12 patients developed human anti-mouse antibodies (HAMA)), heterogenous accumulation throughout the tumor and formation of antibody-soluble CD44 complexes. WO 02/094879 discloses a humanized version of VFF-18 designed to overcome the HAMA response, designated BIWA 4. BIWA 4 was found to have a significantly lower antigen binding affinity than the parent VFF 18 antibody. Surprisingly, the lower affinity BIWA 4 antibody had superior tumor uptake characteristics than the higher affinity BIWA 8 humanized VFF-18 antibody. Both $^{99m}$Technetium-labelled and $^{186}$Rhenium-labelled BIWA 4 antibodies were assessed in a 33 patient Phase 1 clinical trial to determine safety, tolerability, tumor accumulation and maximum tolerated dose, in the case of $^{186}$Re-labelled BIWA 4. There appeared to be tumor relate d uptake of $^{99m}$Tc-labelled BIWA 4. There were no tumor responses seen with all doses of $^{186}$Re-labelled BIWA 4, although a number had stable disease; the dose limiting toxicity occurred at 60 mCi/m$^2$. There was a 50-65 percent rate of adverse events with 12 of 33 patients deemed to have serious adverse events (thrombocytopenia, leucopenia and fever) and of those 6, all treated with $^{186}$Re-labelled BIWA 4, died in the course of treatment or follow-up due to disease progression. Two patients developed human anti-human antibodies (HAHA). A Phase 1 dose escalation trial of $^{186}$Re-labelled BIWA 4 was carried out in 20 patients. Oral mucositis and dose-limiting thrombocytopenia and leucocytopenia were observed; one patient developed a HAHA response. Stable disease was seen in 5 patients treated at the highest dose of 60 mCi/m$^2$. Although deemed to be acceptable in both safety and tolerablility for the efficacy achieved, these studies have higher rates of adverse events compared to other non-radioisotope conjugated biological therapies in clinical studies. U.S. Patent Application U.S. 2003/0103985 discloses a humanized version of VFF-18 conjugated to a maytansinoid, designated BIWI 1, for use in tumor therapy. A humanized VFF 18 antibody, BIWA 4, when conjugated to a toxin, i.e. BIWI 1, was found to have significant anti-tumor effects in mouse models of human epidermoid carcinoma of the vulva, squamous cell carcinoma of the pharynx or breast carcinoma. The unconjugated version, BIWA 4, did not have anti-tumor effects and the conjugated version, BIWI 1, has no evidence of safety or efficacy in humans.

Mab U36 is a murine monoclonal IgG1 antibody generated by UM-SCC-22B human hypopharyngeal carcinoma cell immunization and selection for cancer and tissue specificity. Antigen characterization through cDNA cloning and sequence analysis identified the v6 domain of keratinocyte-specific CD44 splice variant epican as the target of Mab U36. Immunohistochemistry studies show the epitope to be restricted to the cell membrane. Furthermore, Mab U36 labeled 94 percent of the head and neck squamous cell carcinomas (HNSCC) strongly, and within these tumors there was uniformity in cell staining. A 10 patient $^{99m}$Tc-labelled Mab U36 study showed selective accumulation of the antibody to HNSCC cancers (20.4+/− 12.4 percent injected dose/kg at 2 days); no adverse effects were reported but two patients developed HAMA. In a study of radio-iodinated murine Mab U36 there were 3 cases of HAMA in 18 patients and selective homogenous uptake in HNSCC. In order to decrease the antigenicity of Mab U36 and decrease the rate of HAMA a chimeric antibody was constructed. Neither the chimeric nor the original murine Mab U36 has ADCC activity. There is no evidence of native functional activity of Mab U36. $^{186}$Re-labelled chimeric Mab U36 was used to determine the utility of Mab U36 as a therapeutic agent. In this Phase 1 escalating dose trial 13 patients received a scouting dose of $^{99m}$Tc-labelled chimeric Mab U36 followed by $^{186}$Re-labelled chimeric Mab U36. There were no acute adverse events reported but following treatment dose limiting myelotoxcity (1.5 GBq/m$^2$) in 2 of 3 patients, and thrombocytopenia in one patient treated with the maximum tolerated dose (1.0 GBq/m$^2$) were observed. Although there were some effects on tumor size these effects did not fulfill the criteria for objective responses to treatment. A further study of $^{186}$Re-labelled chimeric Mab U36 employed a strategy of using granulocyte colony-stimulating factor stimulated whole blood reinfusion to double the maximum-tolerated activity to 2.8 Gy. In this study of nine patients with various tumors of the head and neck 3 required transfusions for drug related anemia. Other toxicity includes grade 3 myelotoxicity, and grade 2 mucositis. No objective tumor responses were reported although stable disease was achieved for 3-5 months in 5 patients. Thus, it can be seen that although Mab U36 is a highly specific antibody the disadvantage of requiring a radioimmunoconjugate to achieve anticancer effects limits its usefulness because of the toxicity associated with the therapy in relation to the clinical effects achieved.

To summarize, a CD44v6 (1.1ASML) and CD44v10 (K926) monoclonal antibody have been shown to reduce metastatic activity in rats injected with a metastatic pancreatic adenocarcinoma or mice injected with a malignant melanoma respectively. Another anti-CD44v6 antibody (VFF-18 and its derivatives), only when conjugated to a maytansinoid or a radioisotope, has been shown to have anti-tumor effects. Anti-standard CD44 monoclonal antibodies have also been shown to suppress intracerebral progression by rat glioblastoma (anti-CD44s), lymph node invasion by mouse T cell lymphoma (IM-7.8.1) as well as inhibit implantation of a human ovarian cancer cell line in nude mice (clone 515), lung metastasis of a mouse melanoma cell line (IM-7.8.1) and metastasis of a human melanoma cell line in SCID mice (GKW.A3). The radioisotope conjugated Mab U36 anti-CD44v6 antibody and its derivatives had anti-tumor activity in clinical trials that were accompanied by significant toxicity. These results, though they are encouraging and support the development of anti-CD44 monoclonal antibodies as potential cancer therapeutics, demonstrate limited effectiveness, safety, or applicability to human cancers.

Thus, if an antibody composition were isolated which mediated cancerous cell cytotoxicity, as a function of its attraction to cell surface expression of CD44 on said cells, a valuable diagnostic and therapeutic procedure would be realized.

PRIOR PATENTS

U.S. Pat. No. 5,750,102 discloses a process wherein cells from a patient's tumor are transfected with MHC genes, which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies, which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to anti-Her2 antibodies, which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is 2-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an anti-nuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

U.S. Pat. No. 5,916,561 discloses a specific antibody, VFF-18, and its variants directed against the variant exon v6 of the CD44 gene. This antibody is an improvement over the comparator antibody in that it recognizes a human CD44 v6 variant rather than a rat CD44 v6 variant. In addition this antibody discloses diagnostic assays for CD44 v6 expression. There was no in vitro or in vivo function disclosed for this antibody.

U.S. Pat. No. 5,616,468 discloses a monoclonal antibody, Var3.1, raised against a synthetic peptide containing a sequence encoded by the human exon 6A of the CD44 gene. Specifically this antibody does not bind to the 90 kD form of human CD44 and is distinguished from the Hermes-3 antibody. A method for detection of the v6 variant of CD44 is provided, as well as a method for screening and assaying for malignant transformation based on this antigen. A method for screening for inflammatory disease based on detecting the antigen in serum is also provided.

U.S. Pat. No. 5,879,898 discloses a specific antibody that binds to a 129 bp exon of a human CD44 variant 6 that produces a 43 amino acid peptide. The monoclonal antibody is produced by a number of hybridoma cell lines: MAK<CD44>M-1.1.12, MAK<CD44>M-2.42.3, MAK<CD44>M-4.3.16. The antibody is generated from a fusion protein that contains at least a hexapeptide of the novel CD44 v6 amino acid sequence. Further, there is a disclosure of an immunoassay for the detection of exon 6 variant that can be used as a cancer diagnostic. Significantly, there is no in vitro or in vivo function of this antibody disclosed.

U.S. Pat. No. 5,942,417 discloses a polynucleotide that encodes a CD44 like polypeptide, and the method of making a recombinant protein using the polynucleotide and its variants. Antibodies are claimed to these polypeptides however there are no specific examples and there are no deposited clones secreting such antibodies. Northern blots demonstrate the appearance of the polynucleotide in several types of tissues, but there is no accompanying evidence that there is translation and expression of this polynucleotide. Therefore, there is no evidence that there were antibodies to be made to the gene product of this polynucleotide, that these antibodies would have either in vitro or in vivo function, and whether they would be relevant to human cancerous disease.

U.S. Pat. No. 5,885,575 discloses an antibody that reacts with a variant epitope of CD44 and methods of identifying the variant through the use of the antibody. The isolated polynucleotide encoding this variant was isolated from rat cells, and the antibody, mAb 1.1ASML, directed against this variant recognizes proteins of molecular weight 120 kD, 150 kD, 180 kD, and 200 kD. The administration of monoclonal antibody 1.1ASML delayed the growth and metastases of rat BSp73ASML in isogenic rats. Significantly 1.1ASML does not recognize human tumors as demonstrated by its lack of reactivity to LCLC97 human large-cell lung carcinoma. A human homolog was isolated from LCLC97 but no equivalent antibody recognizing this homolog was produced. Thus, although an antibody specific to a variant of rat CD44 was produced and shown to affect the growth and metastasis of rat tumors there is no evidence for the effect the this antibody against human tumors. More specifically the inventors point out that this antibody does not recognize human cancers.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies, which are useful in treating a cancerous disease. For the purpose of this document, the terms "antibody" and "monoclonal antibody" (mAb) may be used interchangeably and refer to intact immunoglobulins produced by hybridomas (e.g. murine or human), immunoconjugates and, as appropriate, immunoglobulin fragments and recombinant proteins derived from said immunoglobulins, such as chimeric and humanized immunoglobulins, F(ab') and F(ab')$_2$ fragments, single-chain antibodies, recombinant immunoglobulin variable regions (Fv)s, fusion proteins etc. It is well recognized in the art that some amino acid sequence can be varied in a polypeptide without significant effect on the structure or function of the protein. In the molecular rearrangement of antibodies, modifications in the nucleic or amino acid sequence of the backbone region can generally be tolerated. These include, but are not limited to, substitutions (preferred are conservative substitutions), deletions or additions. Furthermore, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells, whereby an antibody conjugate is formed.

This application utilizes substantially the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases as well as primary tumors.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies and/or a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

Using substantially the process of U.S. Pat. No. 6,180,357, the mouse monoclonal antibody H460-16-2 was obtained following immunization of mice with cells from a patient's lung tumor biopsy. The H460-16-2 antigen was expressed on the cell surface of a broad range of human cell lines from different tissue origins. The breast cancer cell line MDA-MB-231 (MB-231) and skin cancer cell line A2058 were susceptible to the cytotoxic effects of H460-16-2 in vitro.

The result of H460-16-2 cytotoxicity against MB-231 cells in culture was further extended by its anti-tumor activity towards these cancer cells when transplanted into mice (as disclosed in Ser. No. 10/603,000). Pre-clinical xenograft tumor models are considered valid predictors of therapeutic efficacy.

In the preventative in vivo model of human breast cancer, H460-16-2 treatment was significantly ($p<0.0001$) more effective in suppressing tumor growth during the treatment period than an isotype control antibody, which was identical to H460-16-2 in structure and size but incapable of binding MB-231 cells. At the end of the treatment phase, mice given H460-16-2 had tumors that grew to only 1.3 percent of the control group. During the post treatment follow-up period, the treatment effects of H460-16-2 were sustained and the mean tumor volume in the treated groups continued to be significantly smaller than controls until the end of the measurement phase. Using survival as a measure of antibody efficacy, it was estimated that the risk of dying in the H460-16-2 treatment group was about 71 percent of the antibody buffer control group ($p=0.028$) at 70 days post-treatment. These data demonstrated that H40-16-2 treatment conferred a survival benefit compared to the control-treated groups. H460-16-2 treatment appeared safe, as it did not induce any signs of toxicity, including reduced body weight and clinical distress. Thus, H460-16-2 treatment was efficacious as it both delayed tumor growth and enhanced survival compared to the control-treated groups in a well-established model of human breast cancer.

In addition, H460-16-2 demonstrated anti-tumor activity against MB-231 cells in an established in vivo tumor model (as outlined in Ser. No. 10/603,000). Treatment with H460-16-2 was compared to the standard chemotherapeutic drug, Cisplatin, and it was shown that the Cisplatin and H460-16-2 treatment groups had significantly ($p<0.001$) smaller mean tumor volumes compared with groups treated with either antibody dilution buffer or the isotype control antibody. H460-16-2 treatment mediated tumor suppression that was approximately two-thirds that of cisplatin chemotherapy but without the significant (19.2 percent) weight loss ($p<0.003$) and clinical distress, including 2 treatment-associated deaths, observed with Cisplatin treatment. The anti-tumor activity of H460-16-2 and its minimal toxicity make it an attractive anti-cancer therapeutic agent. In the post-treatment period, H460-16-2 showed a significant survival benefit ($p<0.02$) as the risk of dying in the H460-16-2 group was about half of that in the isotype control antibody group at >70 days after treatment. The observed survival benefit continued past 120 days post-treatment where 100 percent of the isotype control and cisplatin treated mice had died compared to 67 percent of the H460-16-2 treatment group. H460-16-2 maintained tumor suppression by delaying tumor growth by 26 percent compared to the isotype control antibody group. At 31 days post treatment, H460-16-2 limited tumor size by reducing tumor growth by 48 percent compared to the isotype control group, which is comparable to the 49 percent reduction observed at the end of the treatment. In the established tumor model of breast cancer, these results indicated the potential of H460-16-2 to maintain tumor suppression beyond the treatment phase and demonstrated the ability of the antibody to reduce the tumor burden and enhance survival in a mammal.

In addition to the beneficial effects in the established in vivo tumor model of breast cancer, H460-16-2 treatment in combination with a chemotherapeutic drug (Cisplatin) had anti-tumor activity against PC-3 cells in an established in vivo prostate cancer model. Using a paired t-test, H460-16-2 plus Cisplatin treatment was significantly more effective in suppressing tumor growth shortly after the treatment period than buffer control ($p<0.0001$), Cisplatin treatment alone ($p=0.004$) or H460-16-2 treatment alone ($p<0.0001$). At the end of the treatment phase, mice given H460-16-2 plus Cisplatin had tumors that grew to only 28.5 percent of the buffer control group. For PC-3 SCID xenograft models, body weight can be used as a surrogate indicator of disease progression. Mice in all the groups experienced severe weight loss. In this study, mice in all groups showed a weight loss of approximately 23 to 35 percent by the end of the treatment period. The group treated with H460-16-2 showed the smallest degree of weight loss (21.7 percent). After treatment, day 48, there was no significant increase in weight loss associated with the treatment of H460-16-2 and Cisplatin in comparison to buffer control ($p=0.5042$). Thus, H460-16-2 plus Cisplatin treatment was efficacious as it delayed tumor growth compared to the isotype control treated group in a well-established model of human prostate cancer.

In order to validate the H460-16-2 epitope as a drug target, the expression of H460-16-2 antigen in normal human tissues was previously determined (Ser. No. 10/603,000). This work was extended by comparison with the anti-CD44 antibodies; clone L178 (outlined in Ser. No. 10/647,818) and clone BU75 (outlined herein). By IHC staining with H460-16-2, the majority of the tissues failed to express the H460-16-2 antigen, including the cells of the vital organs, such as the liver, kidney (except for marginal staining of tubular epithelial cells), heart, and lung. Results from tissue staining indicated that H460-16-2 showed restricted binding to various cell types but had binding to infiltrating macrophages, lymphocytes, and fibroblasts. The BU75 antibody showed a similar staining pattern. However, there was at least one difference of note; staining of lymphocytes was more intense with BU75 in comparison to H460-16-2.

Localization of the H460-16-2 antigen and determining its prevalence within the population, such as among breast cancer patients, is important in assessing the therapeutic use of H460-16-2 and designing effective clinical trials. To address H460-16-2 antigen expression in breast tumors from cancer patients, tumor tissue samples from 50 individual breast cancer patients were previously screened for expression of the H460-16-2 antigen (Ser. No. 10/603,000) and was compared to L178 (Ser. No. 10/647,818). Current work compared the staining of H460-16-2 to BU75 and the anti-Her2 antibody c-erbB-2. The results of the current study were similar to previous results and showed that 62 percent of tissue samples stained positive for the H460-16-2 antigen while 73 percent of breast tumor tissues were positive for the BU75 epitope. Expression of H460-16-2 within patient samples appeared specific for cancer cells as staining was restricted to malignant cells. H460-16-2 stained 4 of 10 samples of normal tissue from breast cancer patients while BU75 stained 8. Breast tumor expression of both the H460-16-2 and BU75 antigen appeared to be mainly localized to the cell membrane of malignant cells, making CD44 an attractive target for therapy. H460-16-2 expression was further evaluated based on breast tumor expression of the receptors for the hormones estrogen and progesterone, which play an important role in the development, treatment, and prognosis of breast tumors. No correlation was apparent between expression of the H460-16-2 antigen and expression of the receptors for either estrogen or progesterone. When tumors were analyzed based on their stage, or degree to which the cancer advanced, again there was no clear correlation between H460-16-2 antigen expression and tumor stage. Similar results were obtained with BU75. In comparison to c-erbB-2, H460-16-2 showed a completely different staining profile where 52 percent of the breast tumor tissue samples that were positive for the H460-16-2 antigen were negative for Her2 expression indicating a yet unmet targeted therapeutic need for breast cancer patients. There were also differences in the intensity of staining between the breast tumor tissue sections that were positive for both H460-16-2 and Her2. The c-erbB-2 antibody also positively stained one of the normal breast tissue sections.

To further extend the potential therapeutic benefit of H460-16-2, the frequency and localization of the antigen within various human cancer tissues was also previously determined (Ser. No. 10/603,000) and was compared to clone L178 (Ser. No. 10/647,818). The majority of these tumor types were also positive for the L178 antigen. As with human breast tumor tissue, H460-16-2 and L178 localization occurred on the membrane of tumor cells. However, there was substantially more membrane localization with the L178 compared to the H460-16-2 antibody. Also, of the tumor types that were stained by both H460-16-2 and L178, 43 percent of the tissues showed higher intensity staining with the L178 antibody.

There appears to be no form of CD44 that exactly matches the IHC data presented herein based on comparisons with the IHC data from the literature. The standard form of CD44 is normally expressed in the human brain; H460-16-2 antigen is not. Antibodies directed against pan-CD44 isoforms do not stain the liver (including Kuppfer cells) and positively stain the endometrial glands in all phases of the reproductive cycle. The H460-16-2 antigen is clearly present on Kuppfer cells and is only present on the secretory endometrial glands of the reproductive cycle. H460-16-2 antigen is clearly present on tissue macrophages and only the variant forms V4/5 and V8/9 show occasional macrophage staining. The similar yet distinct binding pattern seen with H460-16-2 in comparison to anti-CD44 L178 and now BU75 indicates that the H460-16-2 antigen is an unique epitope of CD44.

As outlined previously (Ser. No. 10/647,818), additional biochemical data also indicated that the antigen recognized by H460-16-2 is one of the forms of CD44. This was supported by studies that showed a monoclonal antibody (L178) reactive against CD44 identifies proteins that were bound to H460-16-2 by immunoprecipitation. Western blotting studies also suggested that the epitope of CD44 recognized by H460-16-2 was not present on v6 or vl O. The H460-16-2 epitope was also distinguished by being carbohydrate and conformation dependent, whereas many anti-CD44 antibodies are directed against peptide portions of CD44. These IHC and biochemical results demonstrated that H460-16-2 binds to a variant of the CD44 antigen. Thus, the preponderance of evidence showed that H460-16-2 mediates anti-cancer effects through ligation of an unique carbohydrate dependent conformational epitope present on a variant of CD44. For the purpose of this invention, said epitope is defined as a "CD44 antigenic moiety" characterized by its ability to bind with a monoclonal antibody encoded by the hybridoma cell line H460-16-2, antigenic binding fragments thereof or antibody conjugates thereof.

In order to further elucidate the mechanism behind H460-16-2's anti-cancer effects, hyaluronic acid (HA) binding assays were performed. It was determined that an average concentration of 1.87 (+/− 1.01) µg/mL of H460-16-2 was required to yield 50 percent adhesion of MDA-MB-231 cells to HA. These results indicated that H460-16-2 interacts with, at least in part, the region(s) on CD44 that are responsible for binding to HA and consequently could be elucidating its anti-cancer effects through down regulation of angiogenesis or tumor invasiveness through the ECM. In addition to the HA binding assays, a cell cycling experiment was performed in order to determine if the H460-16-2 in vitro and in vivo anti-cancer effects were due to regulation of the cell cycle. After 24 hrs and with 20 µg/mL of H460-16-2, there was an increase in the number of MDA-MB-231 apoptotic cells in comparison to the isotype control. This effect also appeared to be dose dependent. Therefore, the efficacy of H460-16-2 might be also due, in whole or in part, to its apoptotic inducing capabilities.

In toto, this data demonstrates that the H460-16-2 antigen is a cancer associated antigen and is expressed in humans, and is a pathologically relevant cancer target. Further, this data also demonstrates the binding of the H460-16-2 antibody to human cancer tissues, and can be used appropriately for assays that can be diagnostic, predictive of therapy, or prognostic. In addition, the cell membrane localization of this antigen is indicative of the cancer status of the cell due to the lack of expression of the antigen in most non-malignant cells, and this observation permits the use of this antigen, its gene or derivatives, its protein or its variants to be used for assays that can be diagnostic, predictive of therapy, or prognostic.

Other studies, involving the use of anti-CD44 antibodies, have limitations of therapeutic potential that is not exhibited by H460-16-2. H460-16-2 demonstrates both in vitro and in vivo anti-tumor activity. Previously described antibodies such MAK<CD44>M-1.1.12, MAK<CD44>M-2.42.3 and MAK<CD44>M-4.3.16 have no in vitro or in vivo cytotoxicity ascribed to them and VFF-18 and Mab U36 shows no intrinsic tumor cytotoxicity. In addition other anti-CD44 antibodies that have shown in vivo tumor effects also have certain limitations that are not evident with H460-16-2. For example, ASML1.1, K926, anti-CD44s and IM-78.1 show in vivo anti-tumor activity against rat, murine, rat and murine tumors grown in xenograft models respectively. H460-16-2 demonstrates anti-tumor activity in a model of human cancer. H460-16-2 is also directed against human CD44 while antibodies such as ASML1.1 recognize only rat CD44. The clone 515 anti-CD44 antibody does inhibit peritoneal tumor implantation of a human ovarian cell line but does not prevent or inhibit tumor growth. H460-16-2 is capable of inhibiting human breast tumor growth in a SCID mouse xenograft model. GKW.A3 is an anti-human CD44 monoclonal antibody capable of inhibiting tumor growth of a human metastasizing melanoma grown in mice in a preventative but not an established model. H460-16-2 has demonstrated significant anti-tumor activity in both preventative and established murine xenograft models of human breast cancer. Consequently, it is quite apparent that H460-16-2 has superior anti-tumor properties in comparison to previously described anti-CD44 antibodies. It has demonstrated both in vitro and in vivo anti-tumor activity on a human breast tumor in SCID mice and is directed against human CD44. It also exhibits activity in a preventative and established (more clinically relevant) model of human breast cancer and it exhibits activity with Cisplatin in an established model of human prostate cancer.

In all, this invention teaches the use of the H460-16-2 antigen as a target for a therapeutic agent, that when administered can reduce the tumor burden of a cancer expressing the antigen in a mammal (thus delaying disease progression), and can also lead to a prolonged survival of the treated mammal. This invention also teaches the use of a CDMAB (H460-16-2), and its derivatives, to target its antigen to reduce the tumor burden of a cancer expressing the antigen in a mammal, and to prolong the survival of a mammal bearing tumors that express this antigen. In addition, this invention teaches that after binding to its antigen, H460-16-2 can interfere with a cancer cell's ability to interact with hyaluronic acid and can also cause a cancer cell to undergo apoptosis. Furthermore, this invention also teaches the use of detecting the H460-16-2 antigen in cancerous cells that can be useful for the diagnosis, prediction of therapy, and prognosis of mammals bearing tumors that express this antigen.

If a patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody-dependent cell-mediated cytotoxicity (ADCC) or complement-dependent cytotoxicity (CDC). For example murine IgM and IgG2a antibodies can activate human complement by binding the C-1 component of the complement system thereby activating the classical pathway of complement activation which can lead to tumor lysis. For human antibodies, the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody mediated cancer cell killing which are more widely accepted. The first is the use of antibodies as a vaccine to induce the body to produce an immune response against the putative antigen that resides on the cancer cell. The second is the use of antibodies to target growth receptors and interfere with their function or to down regulate that receptor so that effectively its function is lost.

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach methods of utilizing the isolated monoclonal antibody or antigen binding fragment thereof encoded by the clone deposited with the ATCC as PTA-4621 for determining a presence of cells which express a CD44 antigenic moiety which specifically binds to an isolated monoclonal antibody or antigen binding fragment thereof encoded by the clone deposited with the ATCC as PTA-4621.

It is yet a further objective of the instant invention to teach methods for enhancing the survival of a patient having a cancerous disease via the use of an isolated monoclonal antibody or antigen binding fragment thereof encoded by the clone deposited with the ATCC as PTA-4621, which antibody specifically binds to a CD44 antigenic moiety.

It is an additional objective of the invention to teach CDMAB and antigen binding fragments thereof.

It is a further objective of the instant invention to produce CDMAB whose cytotoxicity is mediated through ADCC.

It is yet an additional objective of the instant invention to produce CDMAB whose cytotoxicity is mediated through CDC.

It is still a further objective of the instant invention to produce CDMAB whose cytotoxicity is a function of their ability to catalyze hydrolysis of cellular chemical bonds.

A still further objective of the instant invention is to produce CDMAB which are useful in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Example 1

Figure 1:
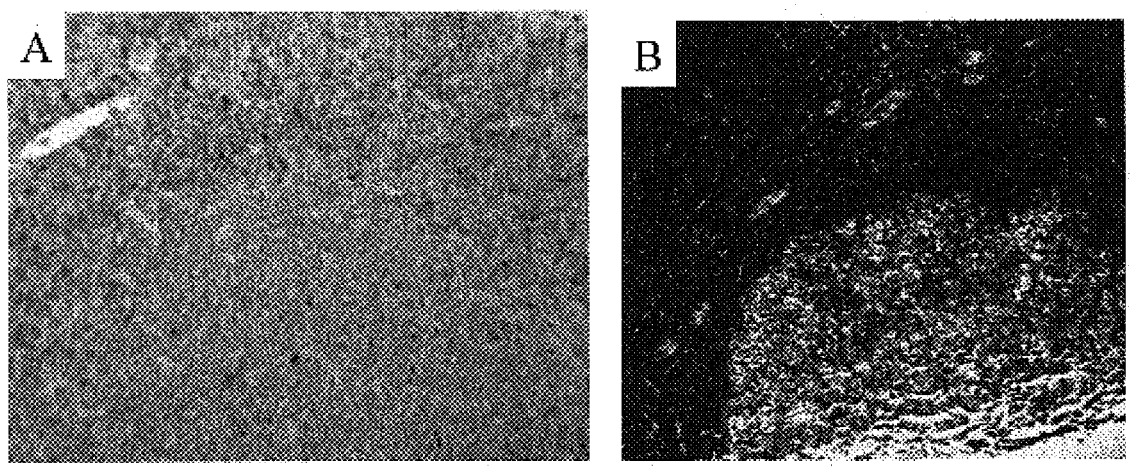
FIG. 1. Representative micrographs showing the binding pattern obtained with H460-16-2 (A) and the anti-CD44 (BU75) antibody (B) on tissues sections of tonsil from a normal human tissue array. There is more intense and widely distributed staining of lymphocytes with BU75 than with H460-16-2. The germinal center (green arrows) had weaker staining for both antibodies. Magnification is 200X.

The hybridoma cell line H460-16-2 was deposited, in accordance with the Budapest Treaty, with the American Type Culture Collection, 10801 University Blvd., Manassas, Va. 20110-2209 on Sep. 4, 2002, under Accession Number PTA-4621. In accordance with 37 CFR 1.808, the depositors assure that all restrictions imposed on the availability to the public of the deposited materials will be irrevocably removed upon the granting of a patent.

Antibody Production:

H460-16-2 monoclonal antibody was produced by culturing the hybridoma in CL-1000 flasks (BD Biosciences, Oakville, ON) with collections and reseeding occurring twice/week. The antibody was purified according to standard antibody purification procedures with Protein G Sepharose 4 Fast Flow (Amersham Biosciences, Baie d'Urfë, QC). It is within the scope of this invention to utilize monoclonal antibodies that are human, humanized, chimerized or murine antibodies.

Example 2

Normal Human Tissue Staining

IHC studies were previously conducted to characterize H460-16-2 antigen distribution in humans (Ser. No. 10/603,000) and in comparison to L178 (Ser. No. 10/647,818). The current studies compare H460-16-2 to another antibody directed against CD44 (BU75) since the H460-16-2 antigen may be a cancer variant of CD44 as determined previously by biochemical methods. Binding of antibodies to 59 normal human tissues was performed using a human normal organ tissue array (Imgenex, San Diego, Calif.). All primary antibodies (H460-16-2; BU75 anti-CD44 (BIOCAN Scientific Inc., Mississauga, ON); and mouse $IgG_1$ negative control (Dako, Toronto, ON)) were diluted in antibody dilution buffer (Dako, Toronto, ON) to a concentration of 5 µg/ml (found to be the optimal concentration in previous optimization steps). The negative control antibody has been shown to be negative to all mammalian tissues by the manufacturer. The procedure for IHC is as follows.

Tissue sections were deparaffinized by drying in an oven at 58° C. for 1 hr and dewaxed by immersing in xylene 5 times for 4 min each in Coplin jars. Following treatment through a series of graded ethanol washes (100%-75%) the sections were re-hydrated in water. The slides were immersed in 10 mM citrate buffer at pH 6 (Dako, Toronto, Ontario) then microwaved at high, medium, and low power settings for 5 min each and finally immersed in cold PBS. Slides were then immersed in 3 percent hydrogen peroxide solution for 6 min, washed with PBS 3 times for 5 min each, dried, incubated with Universal blocking solution (Dako, Toronto, Ontario) for 5 min at room temperature. H460-16-2, BU75 or isotype control antibody (directed towards *Aspergillus niger* glucose oxidase, an enzyme which is neither present nor inducible in mammalian tissues) were diluted in antibody dilution buffer (Dako, Toronto, Ontario) to its working concentration (5 µg/mL for each antibody) and incubated for 1 hr at room temperature. The slides were washed with PBS 3 times for 5 min each. Immunoreactivity of the primary antibodies was detected/visualized with HRP conjugated secondary antibodies as supplied (Dako Envision System, Toronto, Ontario) for 30 min at room temperature. Following this step the slides were washed with PBS 3 times for 5 min each and a color reaction developed by adding DAB (3,3'-diaminobenzidine tetrahydrachloride, Dako, Toronto, Ontario) chromogen substrate solution for immunoperoxidase staining for 10 min at room temperature. Washing the slides in tap water terminated the chromogenic reaction. Following counterstaining with Meyer's Hematoxylin (Sigma Diagnostics, Oakville, ON), the slides were dehyrdated with graded ethanols (75-100%) and cleared with xylene. Using mounting media (Dako Faramount, Toronto, Ontario) the slides were coverslipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a pathologist.

Table 1 presents a summary of the results of H460-16-2 and BU75 anti-CD44 staining of an array of normal human tissues. The staining of tissues with H460-16-2 is similar to that described previously (Ser. No. 10/603,000). It should be again noted that the antigen is generally not present on cells in the vital organs, including the liver, kidney, heart and lung. The H460-16-2 antibody does bind to macrophages and lymphocytes, and their presence is observed in some of the organs in these sections. However, there was a higher intensity of staining of lymphocytes seen with the BU75 anti-CD44 antibody (FIG. 1).

Tissues that were positive for H460-16-2 were also usually positive for BU75 anti-CD44 (sometimes to a greater intensity). Tissues that were negative for H460-16-2 were also generally negative for BU75 anti-CD44 albeit there are a few exceptions such as one sample of esophagus and lymph node. These results demonstrate that H460-16-2 binds to a smaller subset of the tissues recognized by the BU75 anti-CD44 antibody and within tissues the intensity of staining is also sometimes less. These results show that the antigen for H460-16-2 is not widely expressed on normal tissues, and that the antibody binds specifically to a limited number of tissues in humans. It also supports the biochemical data in that H460-16-2 is directed against an epitope of CD44, that is a different variant than the one recognized by the BU75 used for these IHC studies.

TABLE 1

Comparison of BU75 anti-CD44 and H460-16-2 IHC on Human Normal Tissue

| Data Sheet | | BU75 | | H460-16-2 | |
| --- | --- | --- | --- | --- | --- |
| Sec. No. | Organ | Section Score | Tissue specifity | Section Score | Tissue specifity |
| 1 | Skin | +++ | Keratinocytes of all layers except Stratum cornum | +++ | Keratinocytes of all layers except Stratum cornum |
| 2 | Skin | +++ | Keratinocytes of all layers except Stratum cornum | +++ | Keratinocytes of all layers except Stratum cornum |
| 3 | Subcutis fat | – | | – | |
| 4 | Breast | + | Myoepithelium | + | Myoepithelium |
| 5 | Breast | ++ | Ductular epithelium & Myoepithelium | + | Myoepithelium & Fibroblasts |
| 6 | Spleen | +++ | Lymphocytes | ++ | Lymphocytes (more intense in the periarteriolar area) |
| 7 | Spleen | +++ | Lymphocytes (more intense in the periarteriolar area) | +++ | Lymphocytes (more intense in the periarteriolar area) |
| 8 | Lymph node | +++ | Lymphocytes | + | Lymphocytes |
| 9 | Lymph node | + | Lymphocytes | – | |
| 10 | Skeletal muscle | +/– | Blood vessels | +/– | Blood vessels |
| 11 | Nasal Mucosa | +++ | Mucosal epithelium (basal layers) | CD | |
| 12 | Lung | ++ | SMF & Macrophages | ++ | Lymphocytes & Macrophages |
| 13 | Lung | ++ | Aleveolar epithelium & Macrophages | +++ | Lymphocytes & Macrophages |
| 14 | Bronchus | +++ | Chondrocytes | NR | |
| 15 | Heart | – | | – | |
| 16 | Salivary gland | +++ | Ductular & acinar epithelium | ++ | Ductular & acinar epithelium |
| 17 | Liver | +++ | Kupffer cells | +++ | Kupffer cells |
| 18 | Liver | +++ | Kupffer cells | +++ | Kupffer cells |
| 19 | Liver | – | | – | |
| 20 | Gall bladder | +++ | Mucosal basal epithelium & Lymphocytes | + | Mucosal basal epithelium & Lymphocytes |
| 21 | Pancreas | ++ | Acinar epithelium | + | Acinar epithelium |
| 22 | Pancreas | +++ | Acinar epithelium | ++ | Acinar epithelium |
| 23 | Tonsil | +++ | Lymphocytes (less intense at germinal center) | ++ | Lymphocytes (less intense at germinal center) |
| 24 | Esophagus | ++ | Mucosal basal epithelium layers & Lymphocytes | – | |
| 25 | Esophagus | +++ | Basal mucosal epithelial layers & Lymphocytes | +++ | Basal mucosal epithelial layers |
| 26 | Stomach body | +++ | Glandular epithelium in the basal glands & Lmphocytas | ++ | Glandular epithelium in the basal glands & Lmphocytes |
| 27 | Stomach body | +++ | Glandular epithelium in the basal glands & Lymphocytes | +++ | Glandular epithelium in the basal glands & Lymphocytes |
| 28 | Stomach antrum | +++ | Glandular epithelium in the basal glands & Lymphocytes | +++ | Glandular epithelium in the basal glands & Lymphocytes |
| 29 | Stomach smooth muscle | ++ | Blood vessels & Peripheral nerve fibers | ++ | Blood vessels & Fibroblasts |
| 30 | Duodenum | +++ | Lymphocytes in lamina propria | ++ | Lymphocytes in lamina propria |
| 31 | Small bowel | ++ | Glandular epithelium & Lymphocytes | + | Lymphocytes in lamina propria |
| 32 | Small bowel | +++ | Glandular epithelium in the basal glands & Lymphocytes in Lymphoid follicles (Less intense in the germinal center) | +++ | Lymphocytes in Lymphoid follicles (Less intense in the germinal center) |
| 33 | Appendix | +++ | Glandular epithelium in the basal glands & Lymphocytes in Lymphoid follicles (Less intense in the germinal center) | +++ | Lmphocytes in lamina propria +/– Glandular epithelium of basal glands |
| 34 | Colon | +++ | Glandular epithelium in the basal glands & Lymphocytes in | +++ | Lymphocytes & peripheral nerve fibers |

TABLE 1-continued

Comparison of BU75 anti-CD44 and H460-16-2 IHC on Human Normal Tissue

| Data Sheet | | BU75 | | H460-16-2 | |
| --- | --- | --- | --- | --- | --- |
| Sec. No. | Organ | Section Score | Tissue specifity | Section Score | Tissue specifity |
| 35 | Colon | ++ | Lymphoid follicles (Less intense in the germinal center) Lymphocytes & endothelium | +++ | Lymphocytes in lamina propria |
| 36 | Rectum | ++ | Lymphocytes & Endothelium | +++ | Lymphocytes & Fibroblasts |
| 37 | Kidney cortex | ++ | Endothelium of blood vessels | +/− | Interstitial blood vessels |
| 38 | Kidney cortex | +/− | Tubular epithelium | +/− | Tubular epithelium |
| 39 | Kidney Medulla | ++ | Endothelium of blood vessels | +/− | SMF & Fibroblasts |
| 40 | Urinary Bladder | ++ | Transitional epithelium & +/−endothelium of blood vessels | ++ | Lymphocytes & Macrophages Transitional epithelium & endothelium of blood vessels |
| 41 | Prostate | +++ | Myoepithelium | +++ | Myoepithelium |
| 42 | Prostate | +++ | Myoepithelium | ++ | Myoepithelium |
| 43 | Seminal Vesicle | +/− | Endothelium & SMF | +/− | Mucosal epithelium, Endothelium & SMF |
| 44 | Testis | +/− | Endothelium of blood vessels | +/− | Endothelium of blood vessels & fibroblasts |
| 45 | Endometrium proliferative | +++ | Stroma & endothelium of blood vessels & Adjacent myometrium | ++ | Stroma & endothelium of blood vessels & Adjacent myometrium |
| 46 | Endometrium secretory | +++ | Glandular epithelium, Stroma & Endothelium | ++ | Glandular epithelium, Stroma & Endothelium |
| 47 | Myometrium | +++ | SMF | +++ | SMF |
| 48 | Uterine cervix | +++ | Basal layers of mucosal epithelium & Endothelium of blood vessels | +++ | Basal layers of mucosal epithelium |
| 49 | Salpinx | ++ | SMF & endothelium of blood vessels | + | SMF & Fibroblasts |
| 50 | Ovary | ++ | Endothelium & SMF of blood vessels | +/− | SMF of blood vessels |
| 51 | Placenta villi | +/− | Endothelium of blood vessels | +/− | Endothelium of blood vessels |
| 52 | Placenta villi | +/− | Endothelium of blood vessels | +/− | Endothelium of blood vessels |
| 53 | Umbilical cord | − | | − | |
| 54 | Adrenal gland | +/− | Endothelium of blood vessels | +/− | Endocrine glands |
| 55 | Thyroid | +/− | Endothelium of blood vessels | +/− | Parafollicular cells & Endothelium of blood vessels |
| 56 | Thymus | ++ | Lymphocytes | +/− | Lymphocytes |
| 57 | Brain white matter | − | | − | |
| 58 | Brain gray matter | − | | − | |
| 59 | Cerebellum | − | | − | |

Abbreviations: SMF: Smooth muscle fibers, NR: The section is not representative.

Example 3

Human Breast Tumor Tissue Staining

Previous IHC studies were undertaken to determine the cancer association of the H460-16-2 antigen with human breast cancers and whether the H460-16-2 antibody was likely to recognize human cancers (Ser. No. 10/603,000) and how it compared to anti-CD44 staining with L178 (Ser. No. 10/647,818). Currently, a comparison was made for BU75 anti-CD44 staining, c-erbB-2 anti-Her2 and an antibody directed towards *Aspergillus niger* glucose oxidase, an enzyme which is neither present nor inducible in mammalian tissues (negative control). A breast cancer tissue array derived from 50 breast cancer patients and 10 samples derived from non-neoplastic breast tissue in breast cancer patients was used (Imgenex Corporation, San Diego, Calif.). The following information was provided for each patient: age, sex, American Joint Committee on Cancer (AJCC) tumor stage, lymph node, estrogen receptor (ER) and projesterone receptor (PR) status. The procedure for IHC from Example 5 was followed. All antibodies were used at a working concentration of 5 μg/mL except for anti-Her2 which was used at a concentration of 1.5 μg/mL.

Tables 2 and 3 provide summaries of H460-16-2 and BU75 anti-CD44 antibody staining of breast cancer tissue arrays respectively. Each array contained tumor samples from 50 individual patients. Overall, 62 percent of the 50 patients tested were positive for H460-16-2 antigen compared to 73 percent for BU75 anti-CD44. In cases where both H460-16-2 and BU75 anti-CD44 stained the same tissue, 45 percent of the samples had higher intensity staining with the BU75 anti-CD44 in comparison to H460-16-2. For the H460-16-2 and BU75 antigen, 4 and 8 out of 10 normal breast tissue samples from breast cancer patients were positive, respectively. No clear correlation between estrogen and progesterone receptor status was evident. It also did not appear to be a trend to greater positive expression of the H460-16-2 and CD44 antigen with higher tumor stage.

TABLE 2

Human Breast Tumor IHC Summary for H460-16-2

|  |  | Total | Binding Score | | | | | Total Posi- | % Posi- |
|---|---|---|---|---|---|---|---|---|---|
|  |  | # | − | +/− | + | ++ | +++ | tive | tive |
| Patient | Tumor | 50 | 19 | 19 | 4 | 3 | 5 | 31 | 62 |
| Samples | Normal | 10 | 0 | 1 | 0 | 2 | 1 | 4 | 40 |
| ER Status | ER+ | 28 | 13 | 13 | 1 | 1 | 0 | 15 | 54 |
|  | ER− | 22 | 6 | 8 | 3 | 0 | 5 | 16 | 73 |
|  | Unknown | 0 | 0 | 0 | 0 | 0 | 0 | 0 | 0 |
| PR Status | PR+ | 19 | 9 | 8 | 1 | 1 | 0 | 10 | 53 |
|  | PR− | 30 | 8 | 14 | 3 | 0 | 5 | 22 | 73 |
|  | Unknown | 1 | 0 | 1 | 0 | 0 | 0 | 1 | 100 |
| AJCC | T1 | 4 | 2 | 1 | 1 | 0 | 0 | 2 | 50 |
| Tumor | T2 | 21 | 6 | 9 | I | 1 | 4 | 15 | 71 |
| Stage | T3 | 20 | 9 | 9 | 1 | 0 | 1 | 11 | 55 |
|  | T4 | 5 | 2 | 2 | 1 | 0 | 0 | 3 | 60 |

TABLE 3

Human Breast Tumor IHC Summary for Anti-CD44 (BU75)

|  |  | Total | Binding Score | | | | | Total Posi- | % Posi- |
|---|---|---|---|---|---|---|---|---|---|
|  |  | # | − | +/− | + | ++ | +++ | tive | tive |
| Patient | Tumor | 48 | 13 | 6 | 13 | 7 | 9 | 35 | 73 |
| Samples | Normal | 10 | 2 | 0 | 3 | 2 | 3 | 8 | 80 |
| ER Status | ER+ | 27 | 8 | 4 | 10 | 2 | 3 | 19 | 70 |
|  | ER− | 21 | 5 | 2 | 3 | 5 | 6 | 16 | 76 |
|  | Unknown | 0 | 0 | 0 | 0 | 0 | 0 | 0 | 0 |
| PR Status | PR+ | 18 | 4 | 2 | 8 | 2 | 2 | 14 | 78 |
|  | PR− | 29 | 8 | 4 | 5 | 5 | 7 | 21 | 72 |
|  | Unknown | 1 | 1 | 0 | 0 | 0 | 0 | 0 | 0 |
| AJCC | T1 | 4 | 1 | 2 | 0 | 1 | 0 | 3 | 75 |
| Tumor | T2 | 20 | 7 | 0 | 6 | 2 | 5 | 13 | 65 |
| Stage | T3 | 19 | 5 | 2 | 5 | 3 | 4 | 14 | 74 |
|  | T4 | 5 | 0 | 2 | 2 | 1 | 0 | 5 | 100 |

Figure 2:
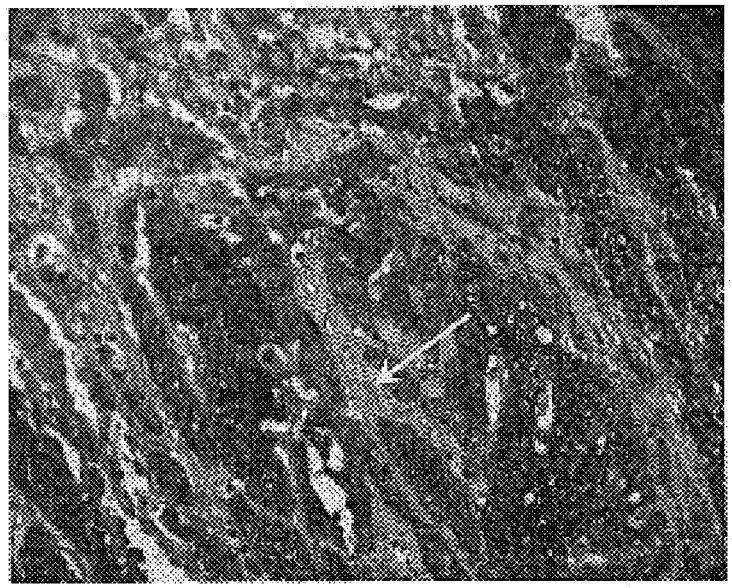
FIG. 2. Representative micrograph of H460-16-2 binding to breast cancer tumor (infiltrating duct carcinoma). The yellow and orange arrows in the panel point to stromal cells and sheets of malignant cells respectively. Magnification is 100X.
Figure 3:
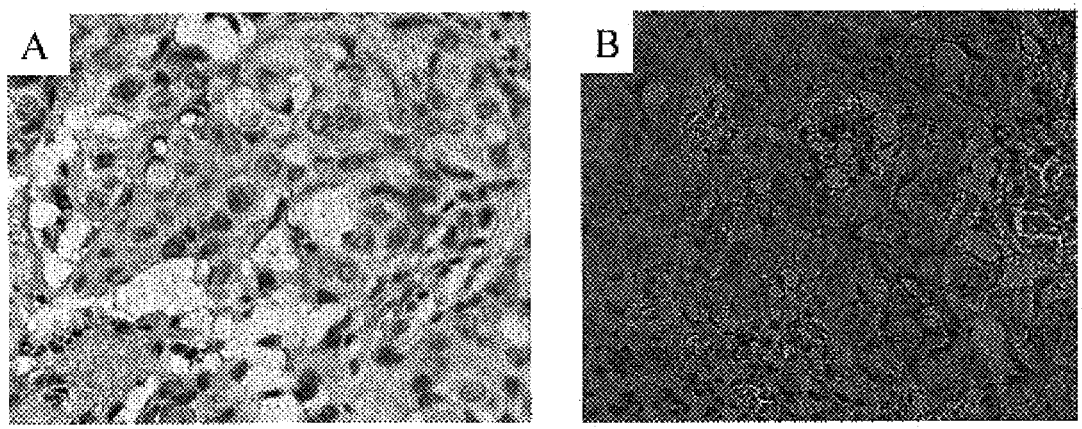
FIG. 3. Representative micrographs showing the binding pattern obtained with H460-16-2 (A) and the anti-CD44 (BU75) antibody (B) on paget's disease breast tissue sections from a human breast cancer tissue array. There is a membranous staining of malignant cells with BU75 versus negative staining with H460-16-2. Magnification is 400X.

The H460-16-2 staining was specific for cancerous cells in comparison to normal cells as demonstrated in FIG. 2 where stromal cells were clearly negative and sheets of malignant cells were highly positive. The cellular localization pattern seen with the H460-16-2 antigen was confined to the cell membrane in the majority of cases. The BU75 CD44 antibody stained more breast cancer samples and showed a higher degree of membrane than cytoplasmic localization compared to H460-16-2 (Table 4). BU75 anti-CD44 also stained malignant cells of Paget's disease, which was not the case for H460-16-2 (FIG. 3). The samples of normal tissue from breast cancer patients that were positive for H460-16-2 staining were also positive for BU75 anti-CD44 staining.

Figure 4:
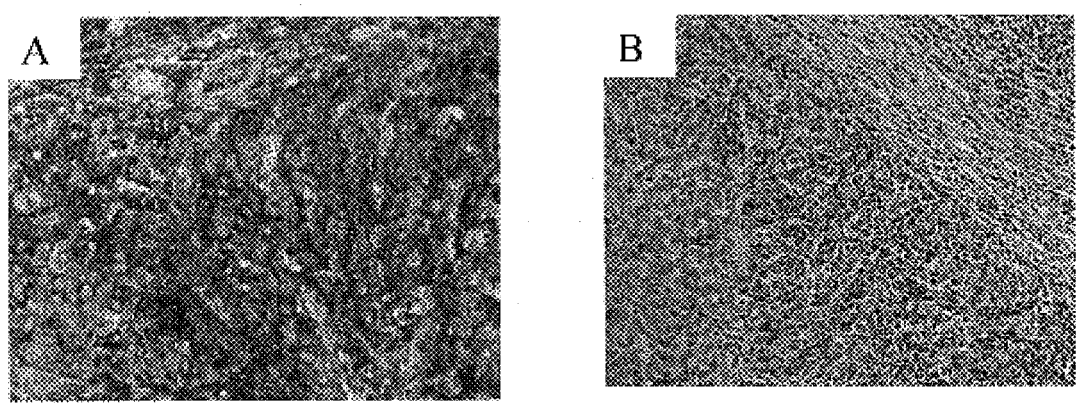
FIG. 4. Representative micrographs showing the binding pattern obtained with H460-16-2 (A) and the anti-Her2 (c-erbB-2) antibody (B) on medullary carcinoma from breast tissue sections from a human breast cancer tissue array. There is strong membranous staining of malignant cells with H460-16-2 versus negative staining with anti-Her2. Magnification is 200X.
Figure 5:
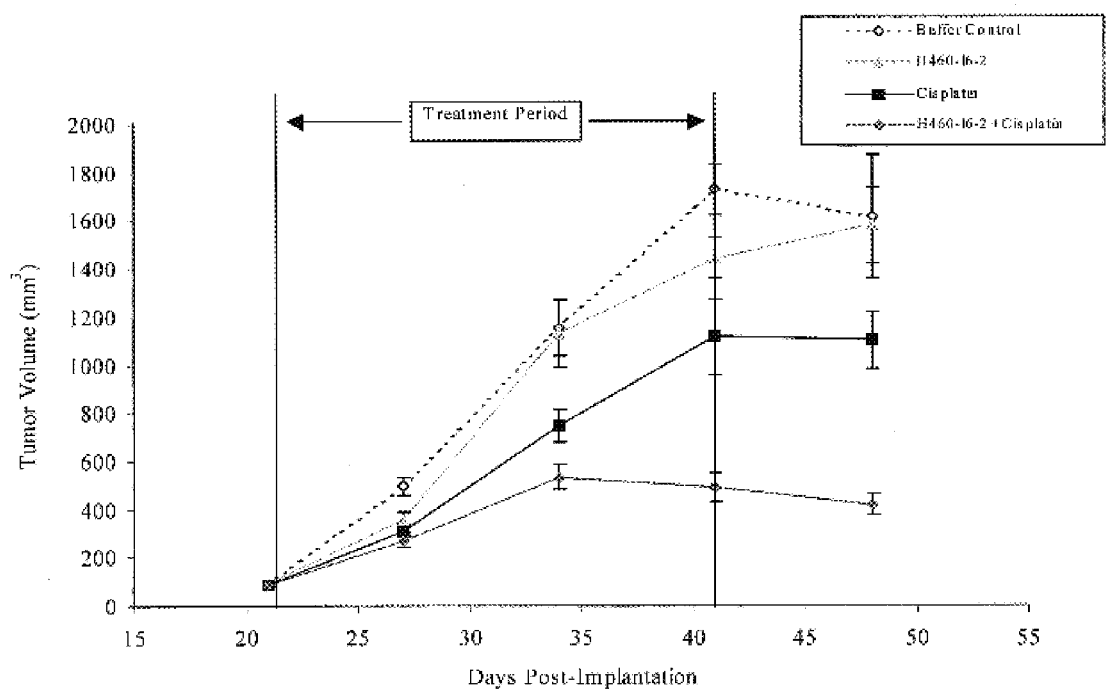
FIG. 5. Effect of H460-16-2, Cisplatin, H460-16-2+Cisplatin or buffer control on tumor growth in an established PC-3 prostate cancer model. The dashed line indicates the period during which the antibody was administered. Data points represent the mean +/- SEM.
Figure 6:
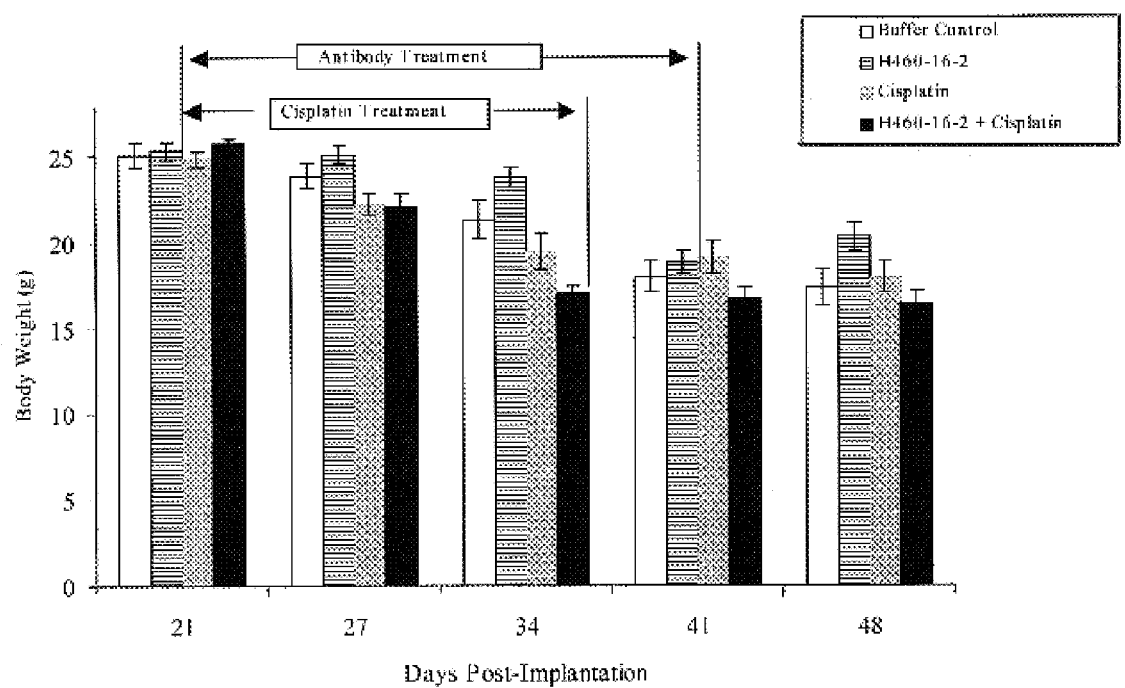
FIG. 6. Effect of H460-16-2, Cisplatin, H460-16-2+Cisplatin or buffer control on body weight in an established PC-3 prostate cancer model.

In comparison to c-erbB-2, H460-16-2 showed a completely different staining profile where 16 out of the 31 breast tumor tissue samples that were positive for the H460-16-2 antigen were negative for Her2 expression indicating a yet unmet targeted therapeutic need for breast cancer patients (Table 5, FIG. 4). There were also differences in the intensity of staining between the breast tumor tissue sections that were positive for both H460-16-2 and Her2; some breast tumor tissue sections that were highly positive for the H460-16-2 antigen were only mildly positive for Her2 and vice versa again illustrating that H460-16-2 would therapeutically target a different cohort of breast cancer patients. The c-erbB-2 antibody also positively stained one of the normal breast tissue sections.

These results suggest the antigen for H460-16-2 may be expressed by almost two thirds of breast cancer patients. In addition, the majority of those suitable for H460-16-2 treatment would not have been suitable for anti-Her2 treatment. The staining pattern showed that in patient samples, the antibody is highly specific for malignant cells and the H460-16-2 antigen is localized to the cell membrane thereby making it an attractive drugable target. The similar albeit more limited staining of H460-16-2 versus BU75 anti-CD44 antibody again demonstrates the likelihood of the H460-16-2 epitope being a more restricted variant of CD44.

TABLE 4

Comparison of BU75 anti-CD44 and H460-16-2 IHC on Human Tumor and Normal Breast Tissue

| Data sheet | | | | BU75 | | H460-16-2 | |
|---|---|---|---|---|---|---|---|
| Sec. No. | Sex | Age | Diagnosis | Section Score | Tissue specificity | Section Score | Tissue specificity |
| 1 | F | 28 | Infiltrating duct carcinoma | +/− | Tumor cells & Stroma | +/− | Tumor cells |
| 2 | F | 71 | Solid papillary carcinoma | + | Tumor cells & Stroma | + | Tumor cells |
| 3 | F | 26 | Infiltrating duct carcinoma | +/− | Tumor cells & Stroma | − | |
| 4 | F | 43 | Infiltrating duct carcinoma | + | Tumor cells | − | |
| 5 | F | 39 | Infiltrating duct carcinoma | +++ | Tumor cells | + | Tumor cells & Necrotic area |
| 6 | F | 46 | Ductal carcinoma in situ | − | | − | |
| 7 | F | 47 | Infiltrating duct carcinoma | +++ | Tumor cells | +++ | Tumor cells |
| 8 | M | 67 | Infiltrating duct carcinoma | + | Tumor cells & Stroma | − | |
| 9 | F | 33 | Infiltrating duct carcinoma | +++ | Tumor cells | − | Tumor cells & Stroma |
| 10 | F | 47 | Infiltrating duct carcinoma | + | Tumor cells & Stroma | + | Tumor cells & Stroma |
| 11 | F | 49 | Invasive Lobular carcinoma | − | | − | |
| 12 | F | 46 | Infiltrating duct carcinoma | + | Tumor cells & Stroma | +/− | Tumor cells & Stroma |
| 13 | F | 39 | Infiltrating duct carcinoma | − | | +/− | |
| 14 | F | 43 | Infiltrating lobular carcinoma | + | Tumor cells | + | Tumor cells |
| 15 | F | 54 | Infiltrating lobular carcinoma | +++ | Tumor cells | +/− | Tumor cells |
| 16 | F | 58 | Infiltrating duct carcinoma | ++ | Tumor cells & Stroma | ++ | Tumor cells |
| 17 | F | 37 | Infiltrating duct carcinoma | − | Tumor's cells +/−Stroma | − | Tumor's cells +/−Stroma |
| 18 | F | 43 | Infiltrating duct carcinoma | +++ | Tumor cells | + | Tumor cells +++Stroma |

TABLE 4-continued

Comparison of BU75 anti-CD44 and H460-16-2 IHC on Human Tumor and Normal Breast Tissue

| | Data sheet | | | BU75 | | H460-16-2 | |
|---|---|---|---|---|---|---|---|
| Sec. No. | Sex | Age | Diagnosis | Section Score | Tissue specificity | Section Score | Tissue specificity |
| 19 | F | 51 | Infiltrating duct carcinoma | +++ | Tumor cells | ++ | Tumor cells |
| 20 | F | 80 | Medullary carcinoma | +++ | Tumor cells & Lymphocytes | +++ | Tumor cells |
| 21 | F | 36 | Infiltrating duct carcinoma | NR | | +++ | Tumor cells |
| 22 | F | 59 | Infiltrating duct carcinoma | + | Tumor cells | +/− | Tumor cells ++Stroma |
| 23 | F | 34 | Ductal carcinoma in situ | + | Tumor cells | +/− | Tumor cells & Necrotic area |
| 24 | F | 54 | Infiltrating duct carcinoma | − | Tumor cells & Stroma | +/− | Tumor cells |
| 25 | F | 47 | Infiltrating duct carcinoma | ++ | Tumor cells | + | Tumor cells |
| 26 | F | 53 | Infiltrating duct carcinoma | + | Tumor cells & Lymphocytes | +/− | Tumor cells ++Stroma |
| 27 | F | 59 | Infiltrating duct carcinoma | + | Tumor cells ++Stroma | +/− | Tumor cells +++Lymphocytes |
| 28 | F | 60 | Signet ring cell carcinoma | F | | − | |
| 29 | F | 37 | Infiltrating duct carcinoma | +/− | Tumor cells & Stroma | | |
| 30 | F | 46 | Infiltrating duct carcinoma | − | Tumor cells +Stroma | +/− | Tumor cells & Stroma |
| 31 | F | 35 | Infiltrating duct carcinoma | − | | − | |
| 32 | F | 47 | Infiltrating duct carcinoma | ++ | Tumor cells | − | Tumor cells +/−Necrotic area |
| 33 | F | 54 | Infiltrating duct carcinoma | + | Tumor cells | − | |
| 34 | F | 47 | Infiltrating duct carcinoma | +++ | Tumor cells | +++ | Tumor cells |
| 35 | F | 41 | Infiltrating duct carcinoma | − | | − | |
| 36 | F | 38 | Infiltrating duct carcinoma | ++ | Tumor cells | + | Tumor cells |
| 37 | F | 55 | Infiltrating duct carcinoma | − | Tumor cells ++Stroma | − | |
| 38 | F | 65 | Infiltrating duct carcinoma | − | Tumor cells ++ Stroma | − | Tumor cells +/−Stroma |
| 39 | M | 66 | Infiltrating duct carcinoma | − | Tumor cells & Necrotic area | − | |
| 40 | F | 44 | Infiltrating duct carcinoma | +/− | Tumor cells & Stroma | − | Tumor cells +Infiltrating Lymphocytes |
| 41 | F | 52 | Metastatic carcinoma in Lymph node | ++ | Tumor cells & Stroma | +/− | Tumor cells & Stroma |
| 42 | F | 32 | Metastatic carcinoma in Lymph node | + | Tumor cells | − | |
| 43 | F | 58 | Metastatic carcinoma in Lymph node | ++ | Tumor cells | ++ | Tumor cells |
| 44 | F | 52 | Metastatic carcinoma in Lymph node | − | | − | |
| 45 | F | 58 | Metastatic carcinoma in Lymph node | − | Tumor cells +++Lymphocytes | +/− | Tumor cells & Lymphocytes |
| 46 | F | 38 | Metastatic carcinoma in Lymph node | +/− | Tumor cells & Lymphocytes | − | Tumor cells + Lymphocytes |
| 47 | F | 45 | Metastatic carcinoma in Lymph node | ++ | Tumor cells | + | Tumor cells |
| 48 | F | 45 | Metastatic carcinoma in Lymph node | + | Tumor cells | +/− | Tumor cells |
| 49 | F | 29 | Metastatic carcinoma in Lymph node | +++ | Tumor cells | +++ | Tumor cells |
| 50 | F | 61 | Metastatic carcinoma in Lymph node | +/− | Tumor cells +++Lymphocytes | +/− | Tumor cells ++Lymphocytes |
| 51 | F | 46 | Nipple | +++ | Keratinocytes (all layers except Stratum cornum) | ++ | Keratinocytes (all layers except Stratum cornum) |
| 52 | F | 47 | Nipple | + | Tumor cells | − | |
| 53 | F | 40 | Normal Breast | ++ | Ductular epithelium | − | |
| 54 | F | 43 | Normal Breast | +++ | Ductular epithelium & Myoepithelium | +++ | Myoepithelium |
| 55 | F | 40 | Normal Breast | ++ | Ductular epithelium & Myoepithelium | ++ | Myoepithelium |
| 56 | F | 40 | Normal Breast | +++ | Myoepithelium +/−Ductular epithelium | +/− | Myoepithelium & Fibroblasts |
| 57 | F | 45 | Normal Breast | − | | − | |
| 58 | F | 44 | Normal Breast | − | | − | |
| 59 | F | 37 | Normal Breast | + | Ductular basement membrane +/−Ductular epithelium | − | |
| 60 | F | 51 | Normal Breast | + | Myoepithelium & Endothelium | −(PD) | |

TABLE 5

Comparison of c-erbB-2 anti-Her2 and H460-16-2 IHC on Human Tumor and Normal Breast Tissue

| | Data sheet | | | c-erbB-2 | | H460-16-2 | |
|---|---|---|---|---|---|---|---|
| Sec. No. | Sex | Age | Diagnosis | Section Score | Tissue specificity | Section Score | Tissue specificity |
| 1 | F | 28 | Infiltrating duct carcinoma | + | Tumor cells | +/− | Tumor cells |
| 2 | F | 71 | Solid papillary carcinoma | − | | + | Tumor cells |
| 3 | F | 26 | Infiltrating duct carcinoma | +/− | Tumor cells | − | |
| 4 | F | 43 | Infiltrating duct carcinoma | +/− | Tumor cells | − | |
| 5 | F | 39 | Infiltrating duct carcinoma | NR | | + | Tumor & Necrotic area |
| 6 | F | 46 | Ductal carcinoma in situ | − | | − | |
| 7 | F | 47 | Infiltrating duct carcinoma | +++ | Tumor cells | +++ | Tumor cells |
| 8 | M | 67 | Infiltrating duct carcinoma | − | | − | |
| 9 | F | 33 | Infiltrating duct carcinoma | +++ | Tumor cells | − | Tumor cells ++Stroma |
| 10 | F | 47 | Infiltrating duct carcinoma | ++ | Tumor cells | + | Tumor cells & Stroma |
| 11 | F | 49 | Invasive Lobular carcinoma | PD | | − | |
| 12 | F | 46 | Infiltrating duct carcinoma | − | | +/− | Tumor cells & Stroma |
| 13 | F | 39 | Infiltrating duct carcinoma | +++ | Tumor cells | − | |
| 14 | F | 43 | Infiltrating lobular carcinoma | − | | + | Tumor cells |
| 15 | F | 54 | Infiltrating lobular carcinoma | − | | +/− | Tumor cells |
| 16 | F | 58 | Infiltrating duct carcinoma | − | | + | Tumor cells ++Necrotic area |
| 17 | F | 37 | Infiltrating duct carcinoma | +++ | Tumor cells | − | Tumor cells +/−Stroma |
| 18 | F | 43 | Infiltrating duct carcinoma | − | | + | Tumor cells +++Stroma |
| 19 | F | 51 | Infiltrating duct carcinoma | + | Tumor cells | ++ | Tumor cells |
| 20 | F | 80 | Medullary carcinoma | − | | +++ | Tumor cells |
| 21 | F | 36 | Infiltrating duct carcinoma | NR | | +++ | Tumor cells & Stroma |
| 22 | F | 59 | Infiltrating duct carcinoma | − | | +/− | Tumor cells |
| 23 | F | 34 | Ductal carcinoma in situ | +++ | Tumor cells | +/− | Tumor's cells & Necrotic area |
| 24 | F | 54 | Infiltrating duct carcinoma | + | Tumor cells | +/− | Tumor cells |
| 25 | F | 47 | Infiltrating duct carcinoma | − | | + | Tumor cells |
| 26 | F | 53 | Infiltrating duct carcinoma | +++ | Tumor cells | +/− | Tumor cells ++Stroma |
| 27 | F | 59 | Infiltrating duct carcinoma | + | Tumor cells | +/− | Tumor cells +++Lymphocytes |
| 28 | F | 60 | Signet ring cell carcinoma | − | | − | |
| 29 | F | 37 | Infiltrating duct carcinoma | +++ | Tumor cells | +/− | Tumor cells |
| 30 | F | 46 | Infiltrating duct carcinoma | − | | +/− | Tumor cells & Stroma |
| 31 | F | 35 | Infiltrating duct carcinoma | − | | − | |
| 32 | F | 47 | Infiltrating duct carcinoma | +++ | Tumor cells | − | Tumor cells +/−Necrotic area |
| 33 | F | 54 | Infiltrating duct carcinoma | − | | − | |
| 34 | F | 47 | Infiltrating duct carcinoma | +++ | Tumor cells | +++ | Tumor cells |
| 35 | F | 41 | Infiltrating duct carcinoma | − | | − | |
| 36 | F | 38 | Infiltrating duct carcinoma | ++ | Tumor cells | + | Tumor cells |
| 37 | F | 55 | Infiltrating duct carcinoma | +/− | Tumor cells | − | |
| 38 | F | 65 | Infiltrating duct carcinoma | − | | − | Tumor cells +/−Stroma |
| 39 | M | 66 | Infiltrating duct carcinoma | − | | − | |
| 40 | F | 44 | Infiltrating duct carcinoma | − | | − | Tumor cells +Infiltrating Lymphocytes |
| 41 | F | 52 | Metastatic carcinoma in Lymph node | − | | +/− | Tumor cells & Stroma |
| 42 | F | 32 | Metastatic carcinoma in Lymph node | − | | − | |
| 43 | F | 58 | Metastatic carcinoma in Lymph node | ++ | Tumor cells | + | Tumor cells |
| 44 | F | 52 | Metastatic carcinoma in Lymph node | +++ | Tumor cells | − | |
| 45 | F | 58 | Metastatic carcinoma in Lymph node | − | | +/− | Tumor cells & Lymphocytes |
| 46 | F | 38 | Metastatic carcinoma in Lymph node | ++ | Tumor cells | − | Tumor cells +Lymphocytes |
| 47 | F | 45 | Metastatic carcinoma in Lymph node | − | | + | Tumor cells |
| 48 | F | 45 | Metastatic carcinoma in Lymph node | − | | +/− | Tumor cells |
| 49 | F | 29 | Metastatic carcinoma in Lymph node | − | | +++ | Tumor cells |
| 50 | F | 61 | Metastatic carcinoma in Lymph node | − | | +/− | Tumor cells ++Lymphocytes |
| 51 | F | 46 | Nipple | − | | ++ | Keratinocytes (all layers except Stratum cornum) |
| 52 | F | 47 | Nipple | +++ | Tumor cells | − | |
| 53 | F | 40 | Normal Breast | − | | − | |
| 54 | F | 43 | Normal Breast | − | | +++ | Myoepithelium |
| 55 | F | 40 | Normal Breast | +/− | Ductular epithelium | ++ | Myoepithelium |
| 56 | F | 40 | Normal Breast | − | | +/− | Myoepithelium & Fibroblasts |
| 57 | F | 45 | Normal Breast | − | | − | |
| 58 | F | 44 | Normal Breast | − | | − | |

TABLE 5-continued

Comparison of c-erbB-2 anti-Her2 and H460-16-2 IHC on Human Tumor and Normal Breast Tissue

| Data sheet | | | | c-erbB-2 | | H460-16-2 | |
| --- | --- | --- | --- | --- | --- | --- | --- |
| Sec. No. | Sex | Age | Diagnosis | Section Score | Tissue specificity | Section Score | Tissue specificity |
| 59 | F | 37 | Normal Breast | – | | – | |
| 60 | F | 51 | Normal Breast | – | | –(PD) | |

Example 4

In Vivo PC-3 Established Chemotherapy Combination Tumor Experiments

With reference to FIGS. 5 and 6, 6 to 8 week old male SCID mice were implanted with 1 million PC-3 human prostate cancer cells in 100 microlitres saline injected subcutaneously in the scruff of the neck. Tumor growth was measured with calipers every week. When the majority of the cohort reached a tumor volume of 80 mm$^3$ (range 50-130 mm$^3$) at 21 days post-implantation, 8 mice were randomly assigned into each of 4 treatment groups. H460-16-2 antibody, the chemotherapeutic drug Cisplatin, the combination of H460-16-2 and Cisplatin or buffer control was administered intraperitoneally with 15 or 6 mg/kg of antibody or Cisplatin respectively at a volume of 300 microliters after dilution from the stock concentration with a diluent that contained 2.7 mM KCl, 1 mM $KH_2PO_4$, 137 mM NaCl and 20 mM $Na_2HPO_4$. H460-16-2 or buffer control was then administered 4 times per week for the first week followed by 3 times per week for 11 doses in total in the same fashion until day 41 post-implantation. Cisplatin was administered on days 0, 5, 10 and 15 of the antibody treatment period. Tumor growth was measured about every seventh day with calipers until day 48 post-implantation or until individual animals reached the CCAC end-points. Body weights of the animals were recorded for the duration of the study. At the end of the study all animals were euthanised according to CCAC guidelines.

Using a paired t-test, there was a post-treatment tumor burden reduction (FIG. 5) associated with treatment with either Cisplatin or the combination of H460-16-2 and Cisplatin. At day 48 (7 days post-treatment) Cisplatin and H460-16-2 treatment was significantly more effective in suppressing tumor growth shortly after the treatment period than buffer control ($p<0.0001$), Cisplatin treatment alone ($p=0.004$) or H460-16-2 treatment alone ($p<0.0001$). PC-3 is a cachexic model of prostate cancer, in which increased tumor burden and disease progression in the xenograft model is accompanied by weight loss. As demonstrated by the mean weights shown in FIG. 6, the mice in all the groups experienced severe weight loss. In this study, mice in all groups showed a weight loss of approximately 23 to 35 percent by the end of the treatment period. The group treated with H460-16-2 showed the smallest degree of weight loss (21.7 percent). Shortly after the end of treatment, there was no additional significant loss of body weight associated with H460-16-2 plus Cisplatin treatment in comparison to the buffer control ($p=0.5042$). Therefore H460-16-2 plus Cisplatin lowered the tumor burden in comparison to a buffer control in a well-recognized model of human breast cancer disease. These results suggest pharmacologic and pharmaceutical benefits of this antibody for cancer therapy in mammals, including man.

Example 5

Hyaluronic Acid (HA) Binding Assay

Figure 7:
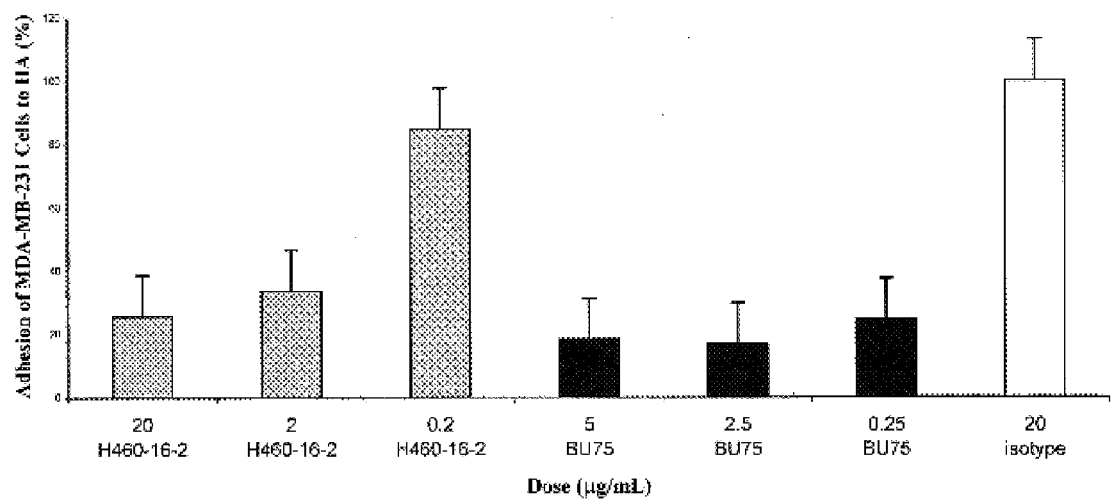
FIG. 7. Effect of H460-16-2, BU75 (positive control) or isotype control on MDA-MB-231 breast cancer cell binding to hyaluronic acid (HA).

MDA-MB-231 cells (shown previously to express the H460-16-2 antigen (CD44) by FACS analysis) were dissociated after aspirating the spent media from the tissue culture plates, washing the plates with PBS, adding 5 mL of dissociation buffer to each plate and incubating the plates at 37° C. until the cells detached. Cells were then counted and collected into 50 mL tube(s). Cells were spun at 1200 rpm for 5 min and resuspended in media to yield 1-5 million cells/mL. One mL was then added to each well of a 2 mL deep well. Cells were pelleted by spinning the plate at 1200 rpm for 5 min and excess supernatant was removed by inverting the plate onto paper towels. Deep well plates were then gently vortexed to dislodge and break up the cell pellets. One mL of H460-16-2, BU75 (positive control, BIOCAN Scientific Inc., Mississauga, ON) or isotype negative control (107.3, BD Biosciences, Oakville, ON) antibody was added to each well and then mixed by gentle vortexing. Plates were then incubated at 37° C. for 2 hrs. Meanwhile, 48-well plates were coated with HA by incubating 300 µl of 4 mg/mL HA stock solution/well for 1-2 hrs at 37° C. After incubation, excess HA was aspirated off and the plates(s) were allowed to completely air dry in the laminar flow hood. After antibody-cell incubation was completed, the cells were again pelleted at 1200 rpm for 5 min. Supernatant was removed by inverting the deep well on paper towels. The deep well was again vortexed to dissociate the cell pellets followed by addition of 1.2 mL of 2 µM calcein-am, in PBS containing $MgCl_2$ and $CaCl_2$, to each well. Cells were resuspended and 250 µl/well was transferred to the HA coated plate. HA coated plates were then incubated at 37° C. for 2 hrs to allow adhesion. After incubation, unattached cells were removed through aspiration. Each well was then washed 2-3 times with PBS containing $MgCl_2$ and $CaCl_2$ in order to remove any unattached cells or cell clumps. The plates were read in a Perkin-Elmer HTS7000 fluorescence plate reader and the data was analyzed in Microsoft Excel and the results were tabulated in Table 6 or FIG. 7. The results from an average of 6 separate experiments revealed that an average of 1.87 (+/– 1.01) µg/mL of H460-16-2 was required in order to cause a 50 percent reduction in the binding of MDA-MB-231 cells to HA (Table 6). The effect of H460-16-2 on MDA-MB-231 cell binding to HA was dose dependent; 20 µg/mL of H460-16-2 resulted in over a 60 percent reduction in cell binding to HA (FIG. 7). These results indicated that H460-16-2 interacts with, at least in part, the region(s) on CD44 that are responsible for binding to HA and consequently could be elucidating its anti-cancer effects through down regulation of angiogenesis or tumor invasiveness through the ECM.

TABLE 6

Summary of Effect of H460-16-2 on MDA-MB-231 Cell Binding to HA

| Experiment | Concentration of Antibody to Yield 50 Percent Adhesion (µg/mL) |
|---|---|
| 1 | 2.42 |
| 2 | 0.99 |
| 3 | 2.56 |
| 4 | 0.70 |
| 5 | 1.87 |
| 6 | 1.06 |
| Average | 1.87 |
| Standard Deviation | 1.01 |

Example 6

Cell Cycling Assay

Figure 8:
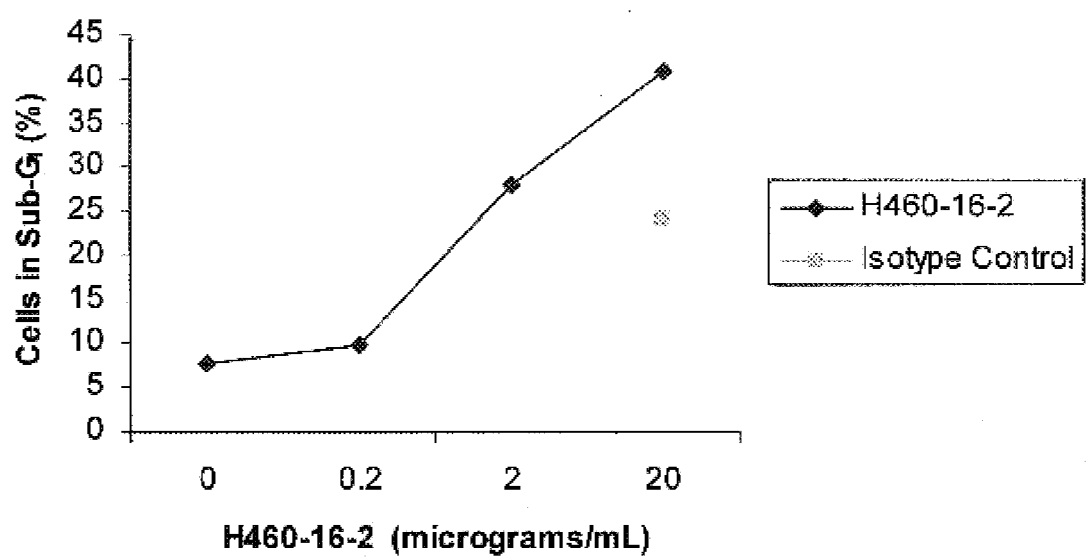
FIG. 8. Effect of H460-16-2 or isotype control on cell cycle distribution of MDA-MB-231 cells after treatment for 24 hrs.

The effect of H460-16-2 on the cell cycle of MDA-MB-231 breast cancer cells was evaluated using FACS analysis. H460-16-2 antibody (0, 0.2, 2.0 and 20 µg/mL) or isotype control (clone 107.3, BD Biosciences, Oakville, ON) was incubated with MDA-MB-231 breast cancer cells for 24, 48 and 72 hrs. Treated and untreated cells were stained with propidium iodide and single cells were analyzed by flow cytometry to assess relative DNA content. The acquired data set was analyzed using BD CellQuest, by gating on the single cells population as well as cells showing hypo-diploid staining. After this analysis, cells treated with H460-16-2 for 24 hrs showed an overall decrease in the percentage of cycling cells as well as a dose dependent increase in the sub-$G_1$ population. Cells that appeared in the sub-$G_1$ population are cells that have lost DNA due to the loss of cell membrane integrity and may represent the apoptotic cell population (FIG. 8). This data demonstrated that H460-16-2 had an effect on MDA-MB-231 cell cycling and this effect led to a dose dependent increase in the number of apoptotic cells.

The preponderance of evidence shows that H460-16-2 mediates anti-cancer effects through ligation of a carbohydrate dependent conformational epitope present on a variant of CD44 and that this epitope is at least partially involved in the binding of CD44 to HA. There is also evidence that binding of H460-16-2 to this epitope can lead to apoptosis on the corresponding cell. It has been shown, in Ser. No. 10/713,451, H460-16-2 antibody can be used to immunoprecipitate the cognate antigen from expressing cells such as MDA-MB-231 cells. Further it could be shown that the H460-16-2 antibody could be used in detection of cells and/or tissues which express a CD44 antigenic moiety which specifically binds thereto, utilizing techniques illustrated by, but not limited to FACS, cell ELISA or IHC.

Thus, it could be shown that the immunoprecipitated H460-16-2 antigen can inhibit the binding of H460-16-2 to such cells or tissues using such FACS, cell ELISA or IHC assays. Further, as with the H460-16-2 antibody, other anti-CD44 antibodies could be used to immunoprecipitate and isolate other forms of CD44 antigen, and the antigen can also be used to inhibit the binding of those antibodies to the cells or tissues that express the antigen using the same types of assays. It could also be shown that if an anti-CD44 antibody that recognizes all forms of CD44 (i.e. a pan-CD44 antibody) were used to isolate its cognate antigen, then that antigen could also inhibit the binding of H460-16-2 antigen to cells or tissues that express that antigen, thus also demonstrating the binding of H460-16-2 to an epitope of CD44 on cells and tissues expressing that antigen. Alternatively, a comparison of H460-16-2 and pan-CD44 antibody in assays such as competitive binding assays. ELISA, cell ELISA, FACS or the like, where both antibodies are present can also demonstrate the binding of H460-16-2 to an epitope of CD44 on cells and tissues expressing that antigen.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of treating a human breast, melanoma or prostate tumor in a mammal, wherein said human tumor expresses at least one epitope of a CD44 antigen which specifically binds to the isolated monoclonal antibody produced by the hybridoma deposited with the ATCC as accession number PTA-4621 or an antigen binding fragment produced from said isolated monoclonal antibody, wherein said antigen binding fragment is characterized by an ability to competitively inhibit binding of said isolated monoclonal antibody to its target antigen, comprising administering to said mammal said monoclonal antibody or said antigen binding fragment in an amount effective to result in a reduction of said mammal's breast, melanoma or prostate tumor burden.

2. The method of claim 1 wherein said isolated monoclonal antibody or said antigen binding fragment is conjugated to a cytotoxic moiety.

3. The method of claim 2 wherein said cytotoxic moiety is a radioactive isotope.

4. The method of claim 1 wherein said isolated monoclonal antibody activates complement.

5. The method of claim 1 wherein said isolated monoclonal antibody mediates cellular cytotoxicity.

6. The method of claim 1 comprising administering a humanized form of the isolated antibody of claim 1, or an antigen binding fragment produced from said humanized form of said isolated antibody.

7. The method of claim 1 comprising administering a chimeric form of the isolated antibody of claim 1, or an antigen binding fragment produced from said chimeric form of said isolated antibody.

8. A method for reduction of human breast, melanoma or prostate tumor burden in a mammal, wherein said human tumor expresses at least one epitope of a CD44 antigen which specifically binds to the isolated monoclonal antibody produced by the hybridoma deposited with the ATCC as accession number PTA-4621 or an antigen binding fragment produced from said isolated monoclonal antibody, wherein said antigen binding fragment is characterized by an ability to competitively inhibit binding of said isolated monoclonal antibody to its target antigen, comprising administering to said mammal said monoclonal antibody or said antigen binding fragment in an amount effective to result in a reduction of said mammal's human breast, melanoma or prostate tumor burden.

9. The method of claim 8 wherein said isolated monoclonal antibody or said antigen binding fragment is conjugated to a cytotoxic moiety.

10. The method of claim 9 wherein said cytotoxic moiety is a radioactive isotope.

11. The method of claim 8 wherein said isolated monoclonal antibody activates complement.

12. The method of claim 8 wherein said isolated monoclonal antibody mediates cellular cytotoxicity.

13. The method of claim 8 comprising administering a humanized form of the isolated antibody of claim 8, or an antigen binding fragment produced from said humanized form of said isolated antibody.

14. The method of claim 8 comprising administering a chimeric form of the isolated antibody of claim 8, or an antigen binding fragment produced from said chimeric form of said isolated antibody.

15. The method of claim 1 wherein said isolated monoclonal antibody or said antigen binding fragment is administered in combination with a chemotherapeutic agent.

16. The method of claim 15, wherein the chemotherapeutic agent is cisplatin.

17. The method of claim 8 wherein said isolated monoclonal antibody or said antigen binding fragment is administered in combination with a chemotherapeutic agent.

18. The method of claim 15, wherein the chemotherapeutic agent is cisplatin.

* * * * *